United States Patent
Harris, III

(10) Patent No.: US 7,799,797 B2
(45) Date of Patent: *Sep. 21, 2010

(54) ARYLSULFONYL NAPHTHALENE DERIVATIVES AND USES THEREOF

(75) Inventor: Ralph New Harris, III, Redwood City, CA (US)

(73) Assignee: Roche Palo Alto LLC, Palo Alto, CA (US)

(*) Notice: Subject to any disclaimer, the term of this patent is extended or adjusted under 35 U.S.C. 154(b) by 602 days.

This patent is subject to a terminal disclaimer.

(21) Appl. No.: 11/820,643

(22) Filed: Jun. 20, 2007

(65) Prior Publication Data

US 2007/0293526 A1 Dec. 20, 2007

Related U.S. Application Data

(60) Provisional application No. 60/815,428, filed on Jun. 20, 2006.

(51) Int. Cl.
- A61K 31/505 (2006.01)
- A61K 31/4166 (2006.01)
- C07D 239/24 (2006.01)
- C07D 233/04 (2006.01)

(52) U.S. Cl. ........ 514/275; 544/224; 544/242; 544/297; 548/316.4; 548/321.5; 548/537; 514/256; 514/385; 514/398

(58) Field of Classification Search ............... 544/224, 544/242, 297; 548/316.4, 321.5, 530, 537; 514/256, 275, 385, 396, 398
See application file for complete search history.

(56) References Cited

U.S. PATENT DOCUMENTS

| | | | |
|---|---|---|---|
| 5,137,901 A | 8/1992 | Junge et al. | |
| 5,374,643 A | 12/1994 | Atwal et al. | |
| 5,412,117 A | 5/1995 | Koga et al. | |
| 5,614,633 A | 3/1997 | Koga et al. | |
| 5,627,138 A | 5/1997 | Anderson et al. | |
| 5,646,308 A | 7/1997 | Koga et al. | |
| 5,663,194 A | 9/1997 | Mewshaw | |
| 5,719,182 A | 2/1998 | Cousins et al. | |
| 5,739,135 A | 4/1998 | Biller et al. | |
| 5,869,478 A | 2/1999 | Ding et al. | |
| 5,874,446 A | 2/1999 | Koga et al. | |
| 5,883,099 A | 3/1999 | Biller et al. | |
| 5,935,958 A | 8/1999 | Kozlowski et al. | |
| 5,977,167 A | 11/1999 | Koga et al. | |
| 6,083,982 A | 7/2000 | Wechter et al. | |
| 6,150,402 A | 11/2000 | Wechter et al. | |
| 6,214,881 B1 | 4/2001 | Xiang | |
| 6,310,107 B1 | 10/2001 | Kato et al. | |
| 6,448,243 B1 | 9/2002 | Kitazawa et al. | |
| 6,479,536 B1 | 11/2002 | Ohkawa et al. | |
| 6,559,144 B2 | 5/2003 | Diefenbach et al. | |
| 6,586,475 B1 | 7/2003 | Kato et al. | |
| 6,605,632 B1 | 8/2003 | Lesieur et al. | |
| 6,613,805 B2 | 9/2003 | Kato et al. | |
| 6,638,972 B2 | 10/2003 | Kelly et al. | |
| 6,660,752 B2 | 12/2003 | O'Connor et al. | |
| 6,706,757 B2 | 3/2004 | Greenblatt et al. | |
| 6,784,314 B2 | 8/2004 | Yamashita et al. | |
| 7,312,359 B2 * | 12/2007 | Greenhouse et al. | 564/147 |
| 7,473,690 B2 * | 1/2009 | Harris et al. | 514/252.12 |
| 7,531,577 B2 * | 5/2009 | Harris et al. | 514/595 |
| 2002/0002177 A1 | 1/2002 | Cousins et al. | |
| 2003/0060498 A1 | 3/2003 | Fu | |
| 2004/0024210 A1 | 2/2004 | Johansson et al. | |
| 2004/0077867 A1 | 4/2004 | Kato et al. | |
| 2004/0087577 A1 | 5/2004 | Pratt et al. | |
| 2004/0097492 A1 | 5/2004 | Pratt et al. | |
| 2004/0162285 A1 | 8/2004 | Pratt et al. | |
| 2004/0167123 A1 | 8/2004 | Pratt et al. | |
| 2005/0075331 A1 | 4/2005 | Pratt et al. | |
| 2005/0154053 A1 | 7/2005 | Rhijn et al. | |
| 2006/0167255 A1 | 7/2006 | Greenhouse et al. | |

FOREIGN PATENT DOCUMENTS

| | | |
|---|---|---|
| EP | 0 488 616 A1 | 6/1992 |
| EP | 0 587 180 A2 | 3/1994 |
| EP | 0 747 374 B1 | 12/1996 |
| WO | WO 97/02259 A1 | 1/1997 |
| WO | WO 98/00412 A1 | 1/1998 |

(Continued)

OTHER PUBLICATIONS

Dhanak, D., et. al., "Identification and Biological Characterization of Heterocyclic Inhibitors of the Hepatitis C Virus RNA-dependent RNA Polymerase," *J. Biological Chem.* (2002) vol. 277, No. 41, pp. 38322-38327.

Gu, B., et. al., "Arresting Initiation of Hepatitis C Virus RNA Synthesis Using Heterocyclic Derivatives," *J. Biological Chem.* (2003) vol. 278, No. 19, pp. 16602-16607.

Nguyen, T. T., et. al. "Resistance Profile of a Hepatitis C Virus RNA-Dependent RNA Polymerase Benzothiadiazine Inhibitor," *Antimicrobial Agents and Chemo.* (2003) vol. 47, No. 11, pp. 3525-3530.

*Primary Examiner*—Golam M Shameem
(74) *Attorney, Agent, or Firm*—Robert C. Hall

(57) ABSTRACT

Compounds of the formula I:

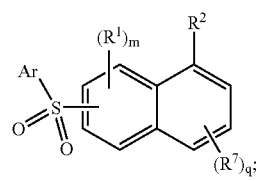

or pharmaceutically acceptable salts thereof,
wherein m, q, Ar, $R^1$, $R^2$ and $R^7$ are as defined herein. Also provided are methods for preparing, compositions comprising, and methods for using compounds of formula I.

20 Claims, No Drawings

FOREIGN PATENT DOCUMENTS

| | | |
|---|---|---|
| WO | WO 01/85172 A1 | 11/2001 |
| WO | WO 03/059356 A2 | 7/2003 |
| WO | WO 03/099801 A1 | 12/2003 |
| WO | WO 04/000828 A1 | 12/2003 |
| WO | WO 2004/058150 A2 | 7/2004 |
| WO | WO 2005/040355 A2 | 5/2005 |
| WO | WO 2005/105776 A1 | 11/2005 |
| WO | WO 2006/059149 A1 | 6/2006 |

* cited by examiner

ARYLSULFONYL NAPHTHALENE DERIVATIVES AND USES THEREOF

CROSS REFERENCE TO RELATED APPLICATIONS

This application claims the benefit of priority of U.S. Provisional Patent Application Ser. No. 60/815,428, filed on Jun. 20, 2006, the disclosure of which is incorporated herein by reference in its entirety.

FIELD OF THE INVENTION

This invention relates to arylsulfonyl naphthalene compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

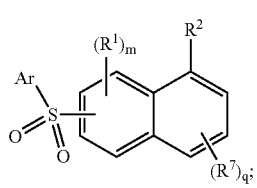

or a pharmaceutically acceptable salt thereof, wherein:
m is from 0 to 3;
q is from 0 to 3;
Ar is optionally substituted aryl or optionally substituted heteroaryl;
$R^1$ and $R^7$ each independently is halo, alkyl, haloalkyl, alkoxy, hydroxy, heteroalkyl, cyano, $-S(O)_t-R^a$, $-C(=O)-NR^bR^c$, $-SO_2-NR^bR^c$, $-N(R^d)-C(=O)-R^e$, or $-C(=O)-R^f$, where t is from 0 to 2, $R^a$, $R^b$, $R^c$, $R^d$ and $R^e$ each independently is hydrogen or alkyl, and $R^f$ is hydrogen, alkyl, alkoxy or hydroxy;
$R^2$ is

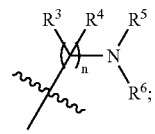

n is from 1 to 3;
$R^3$ and $R^4$ each independently is hydrogen or alkyl, or $R^3$ and $R^4$ together may form =O or =$NR^z$ wherein $R^z$ is hydrogen or alkyl; and
one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; alkylsulfonylalkyl; or optionally substituted heteroaryl; or
$R^5$ and $R^6$ together with the nitrogen to which they are attached may form an amidinyl group, a urea group, a guanidinyl group or a five- or six-membered heteroaryl or heterocyclyl ring that is optionally substituted and which optionally includes an additional heteroatom selected from O, N and S; or
one of $R^5$ and $R^6$ and one of $R^3$ and $R^4$ together with the atoms to which they are attached may form a five- or six-membered ring that optionally includes an additional heteroatom selected from O, N and S.

The invention also provides methods for preparing, methods of using, and pharmaceutical compositions comprising the aforementioned compounds.

DETAILED DESCRIPTION OF THE INVENTION

The invention provides arylsulfonyl naphthalene compounds, associated compositions, methods for use as therapeutic agents, and methods of preparation thereof.

All publications cited in this disclosure are incorporated herein by reference in their entirety.

DEFINITIONS

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Antagonist" refers to a compound that diminishes or prevents the action of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH═CH—), 2,2-dimethylethenylene, propenylene, 2-methylpropenylene, butenylene, pentenylene, and the like.

"Alkylcarbonyl means a group of the formula —C(O)—R wherein R is alkyl as defined herein.

"Alkylcarbonylaminoalkyl" means a group of the formula —R—NR'—R" wherein R is alkylene, R' is hydrogen or alkyl, and R" is alkylcarbonyl as defined herein.

"Alkylsulfonyl" means a group —SO$_2$—R wherein R is alkyl as defined herein.

"Alkylsulfonylalkyl" means a group —R—SO$_2$—R' wherein R' is alkyl and R is alkylene as defined herein.

"Alkylsulfonylalkylaminoalkyl" means a group of the formula —R—NR'—R" wherein R is alkylene, R' is hydrogen or alkyl, and R" is alkylsulfonylalkyl as defined herein.

"Alkylsulfonamidoalkyl" means a group of the formula —R—NR'—SO$_2$—R" wherein R is alkylene, R' is hydrogen or alkyl, and R" is alkyl as defined herein.

"Alkoxy" means a group —OR, wherein R is alkyl as defined herein. Examples of alkoxy moieties include, but are not limited to, methoxy, ethoxy, isopropoxy, and the like.

"Alkoxycarbonyl" means a group of the formula —C(O)—R wherein R is alkoxy as defined herein.

"Alkoxycarbonylaminoalkyl" means a group of the formula —R—NR'—R" wherein R is alkylene, R' is hydrogen or alkyl, and R" is alkoxycarbonyl as defined herein.

"Alkoxycarbonylalkyl" means a group of the formula —R—C(O)—R' wherein R' is alkoxy and R is alkylene as defined herein.

"Alkoxycarbonylalkylaminoalkyl" means a group of the formula —R—NR'—R" wherein R is alkylene, R' is hydrogen or alkyl, and R" is alkoxycarbonyl alkyl as defined herein.

"Alkoxyalkyl" is a group of the formula —R—OR' wherein R' is alkyl and R is alkylene as defined herein.

"Alkoxyalkylaminoalkyl" means a group of the formula —R—NR'—R" wherein R is alkylene, R' is hydrogen or alkyl, and R" is alkoxyalkyl as defined herein.

"Amino" means a group —NRR' wherein R and R' each independently is hydrogen or alkyl as defined herein. "Amino" thus includes "alkylamino" and "dialkylamino".

"Amidinyl" means a group of the formula:

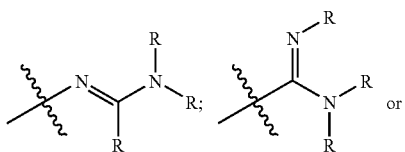

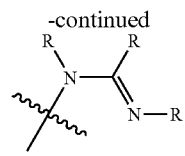

wherein each R independently is hydrogen or alkyl as defined herein. "N-cyanoamidinyl" means a group of the formula

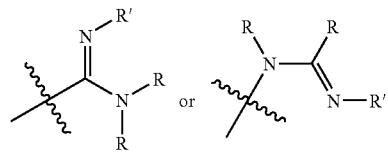

wherein R' is cyano and R is hydrogen or alkyl as defined herein.

"Aminosulfonyl means a group —SO$_2$—R wherein R is —NR'— and R' is hydrogen or alkyl as defined herein.

"Amidinylalkyl" means a group —R—R' wherein R' is amidinyl and R is alkylene as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Alkylaminoalkyl" means a group of the formula —R—NR'—R" wherein R' is hydrogen or alkyl, R" is alkyl, and R is alkylene as defined herein. "Dialkylaminoalkyl" is alkylaminoalkyl wherein R' is alkyl.

"Aminocarbonyl" means a group of the formula —C(O)—R wherein R is amino as defined herein.

"Aminocarbonylalkyl" means a group of the formula —R—C(O)—R' wherein R' is amino and R is alkylene as defined herein.

"Aminocarbonylalkylaminoalkyl means a group of the formula —R—NR'—R" wherein R is alkylene, R' is hydrogen or alkyl, and R" is aminocarbonylalkyl as defined herein.

"Aminoalkylcarbonyl" means a group of the formula —C(O)—R—R' wherein R' is amino and R is alkylene as defined herein.

"Aminoalkylcarbonylaminoalkyl" means a group of the formula —R—NR' R" wherein R is alkylene, R' is hydrogen or alkyl, and R" is aminocarbonylalkyl as defined herein.

"Aminosulfonamidoalkyl" means a group of the formula —R—NR'—SO$_2$—R" wherein R is alkylene, R' is hydrogen or alkyl, and R" is amino as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof. Preferred aryl are phenyl and naphthyl, more preferred is phenyl. Preferred optional substituents are halo, alkyl, haloalkyl, alkoxy, alkylsulfonyl, and cyano. Most preferred optional substituents are fluoro, chloro, methyl, methoxy, trifluoromethyl, methanesulfonyl and cyano.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —R—R' where R is an alkylene group and R' is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Preferably, cycloalkyl means a 3- to 7-membered saturated carbocyclic moiety. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R—R', where R is alkylene and R' is cycloalkyl as defined herein.

"Guanidinyl" means a group of the formula

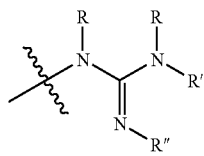

wherein each R independently is hydrogen or alkyl, R' is hydrogen, alkyl, or phenyl, and R" is hydrogen, alkyl or cyano. The phenyl moiety of "guanidinyl" may be optionally substituted as defined herein. "N-cyanoguanidinyl" means R" in the formula for guanidinyl is cyano.

"Guanidinylalkyl" is a group —R—R' wherein R' is guanidinyl and R is alkylene as defined herein. "N-cyanoguanidinylalkyl means R' is N-cyanoguanidinyl as defined herein.

"Guanidinylcarbonylalkyl" means a group of the formula —R—C(O)—R' wherein R' is guanidinyl and R is alkylene as defined herein.

"Heteroalkyl" means an alkyl radical as defined herein wherein one, two or three hydrogen atoms have been replaced with a substituent independently selected from the group consisting of —$OR^{ii}$, —$NR^{iii}R^{iv}$, and —$S(O)_zR^v$ (where z is an integer from 0 to 2), with the understanding that the point of attachment of the heteroalkyl radical is through a carbon atom, wherein $R^{ii}$ is hydrogen, acyl, alkyl, cycloalkyl, or cycloalkylalkyl; $R^{iii}$ and $R^{iv}$ are independently of each other hydrogen, acyl, alkyl, cycloalkyl, or cycloalkylalkyl; and when z is 0, $R^v$ is hydrogen, alkyl, cycloalkyl, or cycloalkylalkyl, and when z is 1 or 2, $R^v$ is alkyl, cycloalkyl, cycloalkylalkyl, amino, acylamino, monoalkylamino, or dialkylamino. Representative examples include, but are not limited to, methoxy, ethoxy, 2-hydroxyethyl, 3-hydroxypropyl, 2-methoxyethyl, 3-methoxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. The aforementioned heteroaryl moieties may be partially saturated. Thus, "heteroaryl" includes "imidazolinyl", tetrahydropyrimidinyl" and the like.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

"Heteroarylaminoalkyl" means a group of the formula —R—NR'—R" wherein R is alkylene, R' is hydrogen or alkyl, and R" is heteroaryl as defined herein.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof. A preferred heterocyclyl is piperazin-2-one.

"Hydroxyalkyl" means an alkyl as defined herein that is substituted one, two or three times with hydroxy.

"Hydroxyalkylcarbonyl" means a group of the formula —C(O)—R—OH wherein R is alkylene as defined herein.

"Hydroxyalkylcarbonylaminoalkyl" means a group of the formula —R—NR'—R" wherein R is alkylene, R' is hydrogen or alkyl, and R" is hydroxyalkylcarbonyl as defined herein.

"Hydroxyalkylaminoalkyl" means a group of the formula —R—NR'—R" wherein R is alkylene, R' is hydrogen or alkyl, and R" is hydroxyalkyl as defined herein.

"Imidazolinyl" means a group of the formula

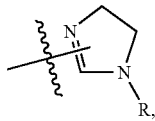

and more preferably a group of the formula

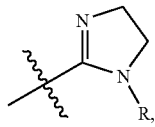

wherein R is hydrogen or alkyl. "Imidazolinyl" may be interchangeably used with "4,5-dihydro-1H-imidazol-2-yl".

"Imidazolonyl" means a group of the formula

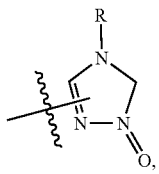

and more preferably a group of the formula

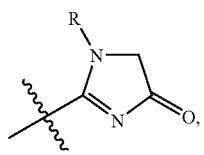

wherein R is hydrogen or alkyl.

"Imidazolonylaminoalkyl means a group of the formula —R—NR'—R" wherein R is alkylene, R' is hydrogen or alkyl, and R" is imidazolonyl as defined herein.

"Imidazolinylalkyl" means a group —R—R' wherein R' is imidazolinyl as defined herein and R is alkylene.

"Imidazolinylaminoalkyl" means a group —R—R'—R" wherein R" is imidazolinyl as defined herein, R' is amino, and R is alkylene. The amino moiety of "imidazolinylaminoalkyl" may be optionally substituted with alkyl.

"Imidazolylcarbonyl" means a group of the formula

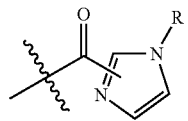

wherein R is hydrogen or alkyl as defined herein.

"Imidazolinylaminoalkyl" means a group of the formula —R—NR'—R" wherein R is alkylene, R' is hydrogen or alkyl, and R" is imidazolinyl as defined herein.

"Imidazolylaminoalkyl" means a group of the formula —R—NR'—R" wherein R is alkylene, R' is hydrogen or alkyl as defined herein, and R" is imidazolyl.

"Imidazolinylalkyl" is a group of the formula —R—R" wherein R is alkylene and R" is imidazolinyl as defined herein "Imidazolinylcarbonylaminoalkyl" means a group of the formula —R—C(O)—NR'—R" wherein R is alkylene, R' is hydrogen or alkyl, and R" is imidazolinyl as defined herein.

"Pyrimidinylaminoalkyl" means a group —R—R'—R" wherein R" is pyrimidinyl (preferably pyrimidin-2-yl), R' is amino, and R is alkylene. The pyrimidinyl moiety of "pyrimidinylaminoalkyl" may be optionally substituted as defined herein, and the amino moiety of "pyrimidinylaminoalkyl" may be optionally substituted with alkyl.

"Pyrrolylcarbonyl" means a group of the formula

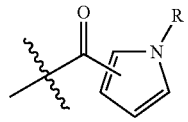

wherein R is hydrogen or alkyl as defined herein.

"Pyrrolylcarbonylaminoalkyl" means a group of the formula —R—NR'—R" wherein R is alkylene, R' is hydrogen or alkyl, and R" is pyrrolylcarbonyl as defined herein.

"Pyrrolidinylcarbonyl" means a group of the formula

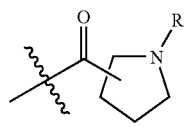

wherein R is hydrogen or alkyl as defined herein.

"Pyrrolidinylcarbonylaminoalkyl" means a group of the formula —R—NR'—R" wherein R is alkylene, R' is hydrogen or alkyl, and R" is pyrrolidinylcarbonyl as defined herein.

"Tetrahydropyrimidinyl" means 1,4,5,6-tetrahydropyrimidinyl, preferably 1,4,5,6-tetrahydropyrimidin-2-yl, and may be optionally substituted as defined herein. "Tetrahydropyrimidinyl" includes 5,5-dimethyl-1,4,5,6-tetrahydropyrimidin-2-yl.

"Tetrahydropyrimidinylaminoalkyl" means a group —R—NR'—R" wherein R" is tetrahydropyrimidinyl, R' is hydrogen or alkyl, and R is alkylene as defined herein.

"Urea" or "ureyl", which may be used interchangeably, means a group of the formula:

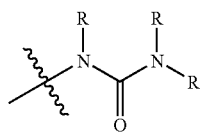

wherein each R is independently is hydrogen or alkyl.

"Urealkyl" means a group R—R' wherein R' is urea and R is alkylene as defined herein.

"Optionally substituted", when used in association with "aryl", "phenyl", "heteroaryl", or "heterocyclyl", means an aryl, phenyl, heteroaryl, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_y$—COOR (where y is an integer from 0 to 5, R' and R" are independently hydrogen or alkyl, and R is hydrogen, alkyl, cycloalkyl, cycloalkylalkyl, phenyl or phenylalkyl), or —(CR'R")$_y$—CONR'''R'''' (where y is an integer from 0 to 5, R' and R" are independently hydrogen or alkyl, and R''' and R'''' are, independently of each other, hydrogen, alkyl, cycloalkyl, cycloalkylalkyl, phenyl or phenylalkyl. Preferred optional substituents, unless specified otherwise, are halo, alkyl, haloalkyl, alkoxy, alkylsulfonyl, and cyano. Most preferred optional substituents, unless specified otherwise, are fluoro, chloro, methyl, methoxy, trifluoromethyl, methanesulfonyl and cyano.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elesevier, N.Y.-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Those skilled in the art know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this application is based on AUTONOM™ v.4.0, a Beilstein Institute computerized system for the generation of IUPAC systematic nomenclature.

Chemical structures shown herein were prepared using ISIS® version 2.2. Any open valency appearing on a carbon, oxygen, sulfur or nitrogen atom in the structures herein indicates the presence of a hydrogen. Where a chiral center exists in a structure and no stereochemistry is indicated, the structure is intended to encompass both stereoisomers associated with the chiral center. Where multiple tautomeric forms of a structure are possible, it is intended that the structure encompass such additional tautomeric forms.

Compounds of the Invention

The invention provides compounds of the formula I:

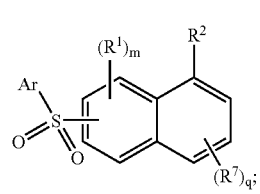

or a pharmaceutically acceptable salt thereof, wherein:

m is from 0 to 3;

q is from 0 to 3;

Ar is optionally substituted aryl or optionally substituted heteroaryl;

$R^1$ and $R^7$ each independently is halo, alkyl, haloalkyl, alkoxy, hydroxy, heteroalkyl, cyano, —S(O)$_t$—R$^a$, —C(=O)—NR$^b$R$^c$, —SO$_2$—NR$^b$R$^c$, —N(R$^d$)—C(=O)—R$^e$, or —C(=O)—R$^f$, where t is from 0 to 2, R$^a$, R$^b$, R$^c$, R$^d$ and R$^e$ each independently is hydrogen or alkyl, and R$^f$ is hydrogen, alkyl, alkoxy or hydroxy;

$R^2$ is

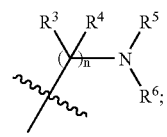

n is from 1 to 3;

$R^3$ and $R^4$ each independently is hydrogen or alkyl, or $R^3$ and $R^4$ together may form =O or =NR$^z$ wherein R$^z$ is hydrogen or alkyl; and one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; alkylsulfonylalkyl; or optionally substituted heteroaryl; or $R^5$ and $R^6$ together with the nitrogen to which they are attached may form an amidinyl group, a urea group, a guanidinyl group or a five- or six-membered heteroaryl or heterocyclyl ring that is optionally substituted and which optionally includes an additional heteroatom selected from O, N and S; or one of $R^5$ and $R^6$ and one of $R^3$ and $R^4$ together with the atoms to which they are attached may form a five- or six-membered ring that optionally includes an additional heteroatom selected from O, N and S.

It should be understood that the scope of this invention encompasses not only the various isomers which may exist but also the various mixture of isomers which may be formed.

Furthermore, the scope of the present invention also encompasses solvates and salts of compounds of formula I:

In many embodiments of formula I, m is 0 or 1.

In certain embodiments of formula I, $R^1$ is halo.

In certain embodiments of formula I, the group Ar—$SO_2$— is located at the 6- or 7-position (with respect to $R^2$) of the naphthalene ring system.

In certain embodiments of formula I, the group Ar—$SO_2$— is located at the 6-position (with respect to $R^2$) of the naphthalene ring system.

In certain embodiments of formula I, m is 0 or 1 and $R^1$ is located at the 8-position of the naphthalene ring system.

In certain embodiments of formula I, n is 1.

In certain embodiments of formula I, n is 2.

In certain embodiments of formula I, n is 3.

Where n is 2 or 3, one $R^3$ may be selected independently from another $R^3$, and one $R^4$ may also be selected independently from another $R^4$.

In certain embodiments of formula I, $R^3$ and $R^4$ are hydrogen, or $R^3$ and $R^4$ together may form =O.

In certain embodiments of formula I, $R^3$ and $R^4$ are hydrogen.

In certain embodiments of formula I, one of $R^5$ and $R^6$ is hydrogen and the other is alkyl.

In certain embodiments of formula I, q is 0.

In certain embodiments of formula I, $R^5$ and $R^6$ are hydrogen.

In certain embodiments of formula I, one of $R^5$ and $R^6$ is hydrogen or alkyl and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of formula I, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of formula I, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of formula I, $R^5$ and $R^6$ together with the nitrogen to which they are attached form an amidinyl group.

In certain embodiments of formula I, $R^5$ and $R^6$ together with the nitrogen to which they are attached form a guanidinyl group.

In certain embodiments of formula I, $R^5$ and $R^6$ together with the nitrogen to which they are attached form a urea group.

In certain embodiments of formula I, $R^3$ and $R^4$ together with the nitrogen to which they are attached form =$NR^z$ wherein $R^z$ is hydrogen.

In certain embodiments of formula I, $R^3$ and $R^4$ together with the nitrogen to which they are attached form =O.

In certain embodiments of formula I, one of $R^5$ and $R^6$ and one of $R^3$ and $R^4$ together with the atoms to which they are attached form an imidazolinyl ring.

In certain embodiments of formula I, $R^5$ and $R^6$ together with the nitrogen to which they are attached form or a five- or six-membered heteroaryl ring that is optionally substituted and which optionally includes an additional nitrogen heteroatom.

In certain embodiments of formula I, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of formula I, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of formula I, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of formula I, Ar is optionally substituted phenyl.

In certain embodiments of formula I, Ar is 2-halophenyl or 3-halopheny.

In certain embodiments of formula I, Ar is heteroaryl.

In certain embodiments of formula I, Ar is heteroaryl selected from indolyl, pyrrolyl, imidazolyl, pyrazolyl, benzimidazolyl, thienyl, furanyl, pyridinyl and pyrimidinyl, each optionally substituted.

In certain embodiments of formula I, Ar is heteroaryl selected from indolyl, pyrrolyl, imidazolyl, pyrazolyl, and benzimidazolyl, each optionally substituted.

In certain embodiments of formula I, Ar is heteroaryl selected from indol-3-yl, pyrrol-3-yl, 1-methylimidazol-2-yl, imidazol-2-yl, pyrazol-4-yl, benzimidazol-4-yl, 6-fluoroindol-3-yl, 1-methylpyrrol-3-yl and 6-fluorobenzimidazol-4-yl.

In certain embodiments of formula I, one of $R^5$ and $R^6$ and one of $R^3$ and $R^4$ together with the atoms to which they are attached form an imidazolinyl ring.

In certain embodiments of formula I, q is 0 and m is 0 or 1.

In certain embodiments of formula I, q is 0, m is 0 or 1, and n is 1.

In certain embodiments of formula I, q is 0, m is 0 or 1, n is 1, and $R^3$ and $R^4$ are hydrogen.

In certain embodiments of formula I, q is 0, m is 0 or 1, $R^3$ and $R^4$ are hydrogen, one of $R^5$ and $R^6$ is hydrogen or alkyl, and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, q is 0, m is 0 or 1, n is 1, $R^3$ and $R^4$ are hydrogen, one of $R^5$ and $R^6$ is hydrogen or alkyl, and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, q is 0, m is 0 or 1, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, q is 0, m is 0 or 1, n is 1, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, q is 0, m is 0 or 1, $R^3$ and $R^4$ are hydrogen, one of $R^5$ and $R^6$ is hydrogen and the other is alkyl.

In certain embodiments of formula I, q is 0, m is 0 or 1, n is 1, $R^3$ and $R^4$ are hydrogen, one of $R^5$ and $R^6$ is hydrogen and the other is alkyl.

In certain embodiments of formula I, q is 0, m is 0 or 1 and $R^2$ is: aminoalkyl; alkylaminoalkyl; dialkylaminoalkyl; imidazolinylaminoalkyl; imidazolinylalkyl, guanidinylalkyl; tetrahydropyrimidinylaminoalkyl; amidinylalkyl; urealkyl; amidinyl; heteroarylaminoalkyl; imidazolylaminoalkyl; guanidinylcarbonylalkyl; imidazolonylaminoalkyl; imidazolinylcarbonylaminoalkyl; aminocarbonylalkyl; pyrrolylcarbonylaminoalkyl; aminoalkylcarbonylaminoalkyl; alkoxycarbonylalkylaminoalkyl; N-cyanoguanidinylalkyl; alkylcarbonylaminoalkyl; aminocarbonylalkylaminoalkyl; pyrrolidinylcarbonylaminoalkyl; alkylsulfonamidoalkyl; aminosulfonamidoalkyl; alkoxycarbonylaminoalkyl; hydroxyalkylcarbonylaminoalkyl; hydroxyalkylaminoalkyl; alkoxyalkylaminoalkyl; or alkylsulfonylalkylaminoalkyl.

In certain embodiments of formula I, q is 0, m is 0 or 1, and $R^2$ is: aminoalkyl; alkylaminoalkyl; dialkylaminoalkyl; guanidinylalkyl; amidinylalkyl; urealkyl; amidinyl; guanidinylcarbonylalkyl; aminocarbonylalkyl; aminoalkylcarbonylaminoalkyl; alkylcarbonylaminoalkyl; aminocarbonylalkylaminoalkyl; or alkoxycarbonylaminoalkyl.

In certain embodiments of formula I, $R^2$ is aminomethyl or aminoethyl wherein the amino is optionally substituted with alkyl, acetyl, aminocarbonyl or alkylsulfonyl.

In certain embodiments of formula I, $R^2$ is aminomethyl or aminoethyl wherein the amino is optionally substituted with methyl, acetyl, aminocarbonyl, methanesulfonyl or ethanesulfonyl.

In certain embodiments of formula I, q is 0, m is 0 or 1, and $R^2$ is:

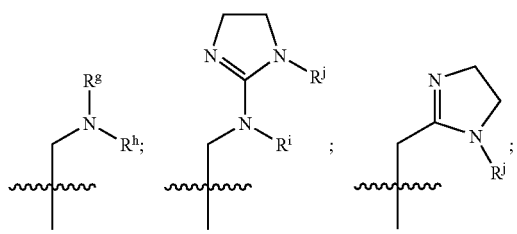

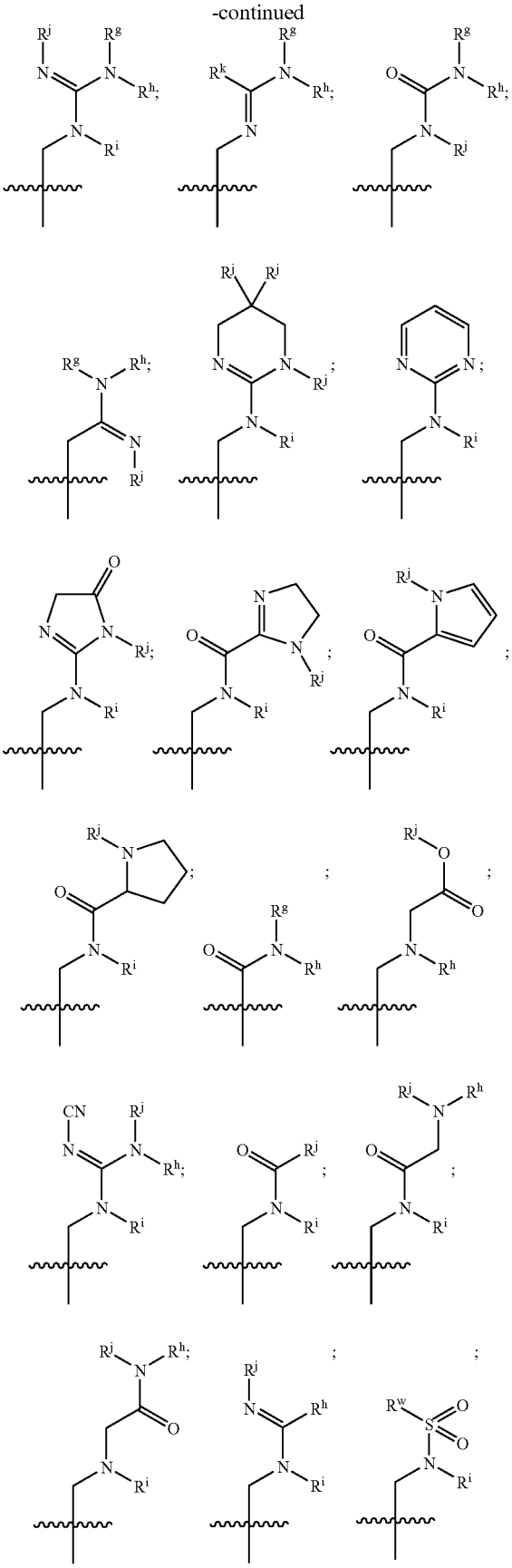

-continued

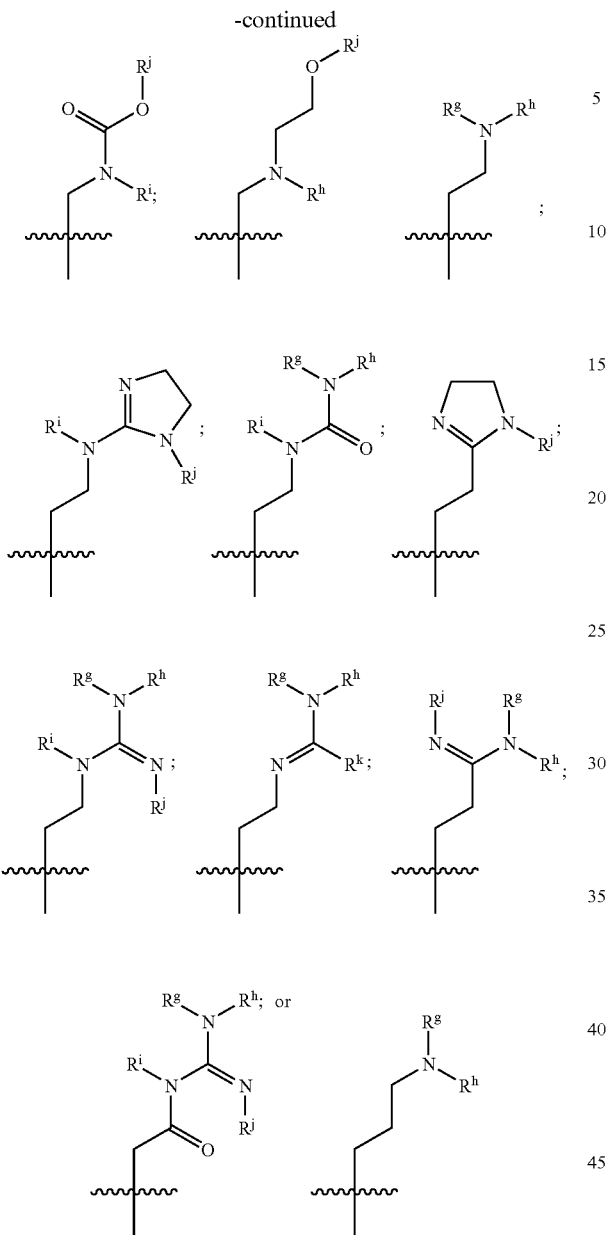

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula I, $R^2$ is:

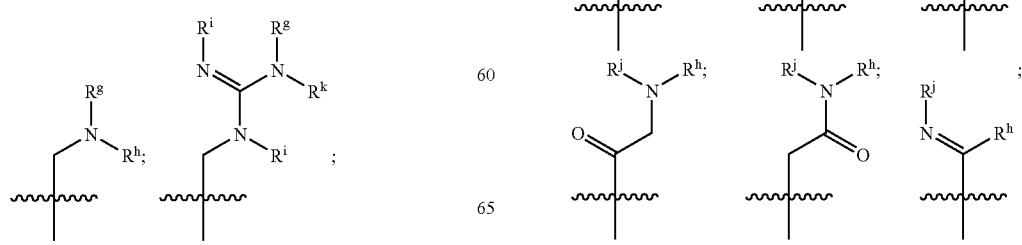

-continued wherein $R^h$ is hydrogen, alkyl or alkylsulfonyl, $R^j$ is hydrogen, alkyl or amino, and $R^g$, $R^i$ and $R^k$ $R^g$, $R^h$, $R^i$ and $R^j$ are hydrogen or alkyl.

In certain embodiments of formula I, q is 0, m is 0 or 1, n is 1, $R^3$ and $R^4$ are hydrogen, one of $R^5$ and $R^6$ is hydrogen or alkyl, and the other is:

-continued

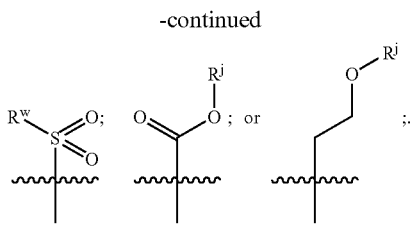

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^h R^i$.

In certain embodiments of formula I, q is 0, m is 0 or 1, $R^3$ and $R^4$ are hydrogen, one of $R^5$ and $R^6$ is hydrogen or alkyl, and the other is:

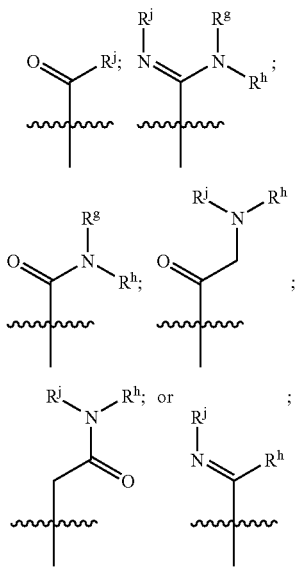

wherein $R^g$, $R^h$, $R^i$ and $R^j$ are hydrogen or alkyl.

In certain embodiments of formula I, q is 0, m is 0 or 1, n is 1, $R^3$ and $R^4$ are hydrogen, one of $R^5$ and $R^6$ is hydrogen or alkyl, and the other is:

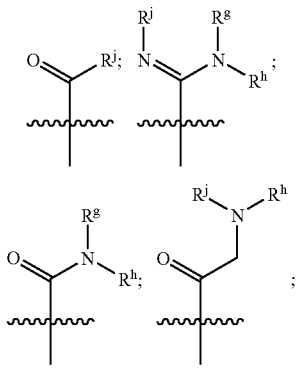

wherein $R^g$, $R^h$, $R^i$ and $R^j$ are hydrogen or alkyl.

-continued

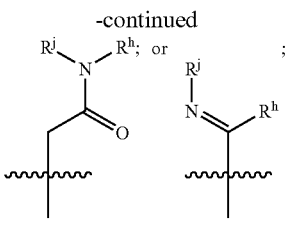

wherein $R^g$, $R^h$, $R^i$ and $R^j$ are hydrogen or alkyl.

In certain embodiments of formula I, q is 0, m is 0 or 1, $R^3$ and $R^4$ together with the nitrogen to which they are attached form =$NR^z$ wherein $R^z$ is hydrogen, and wherein $R^5$ and $R^6$ are hydrogen.

In certain embodiments of formula I, q is 0, m is 0 or 1, and $R^3$ and $R^4$ together with the nitrogen to which they are attached form =O.

In certain embodiments of formula I, q is 0, m is 0 or 1, and n is 2.

In certain embodiments of formula I, q is 0, m is 0 or 1, n is 2, and $R^3$ and $R^4$ are hydrogen.

In certain embodiments of formula I, q is 0, m is 0 or 1, n is 2, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, q is 0, m is 0 or 1, n is 2, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, q is 0, m is 0 or 1, n is 2, $R^3$ and $R^4$ are hydrogen, one of $R^5$ and $R^6$ is hydrogen and the other is alkyl.

In certain embodiments of formula I, q is 0, m is 0 or 1, n is 2, $R^3$ and $R^4$ are hydrogen, one of $R^5$ and $R^6$ is hydrogen or alkyl, and the other is:

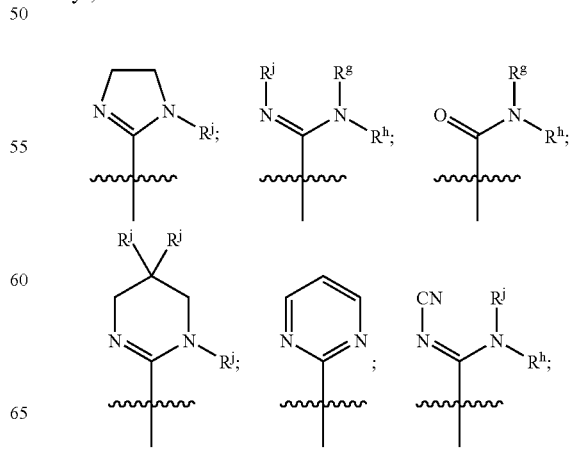

-continued

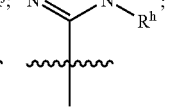

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula I, q is 0, m is 0 or 1, n is 2, $R^3$ and $R^4$ are hydrogen, one of $R^5$ and $R^6$ is hydrogen or alkyl, and the other is:

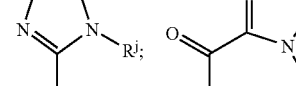

wherein $R^g$, $R^h$, $R^i$ and $R^j$ are hydrogen or alkyl.

In certain embodiments of formula I, q is 0, m is 0 or 1, and n is 3.

In certain embodiments of formula I, q is 0, m is 0 or 1, n is 1, and $R^3$ and $R^4$ are hydrogen.

In certain embodiments of formula I, q is 0, m is 0 or 1, n is 3, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, q is 0, m is 0 or 1, n is 3, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, q is 0, m is 0 or 1, n is 3, $R^3$ and $R^4$ are hydrogen, one of $R^5$ and $R^6$ is hydrogen or alkyl, and the other is:

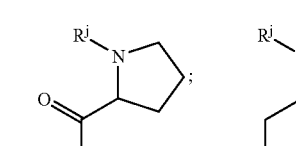

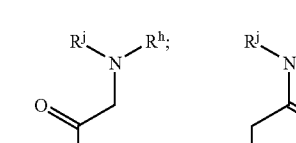

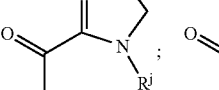

-continued

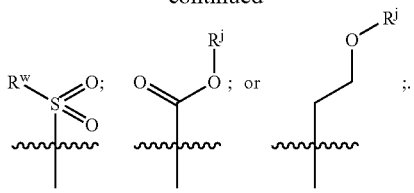

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula I, q is 0, m is 0 or 1, n is 3, $R^3$ and $R^4$ are hydrogen, one of $R^5$ and $R^6$ is hydrogen or alkyl, and the other is:

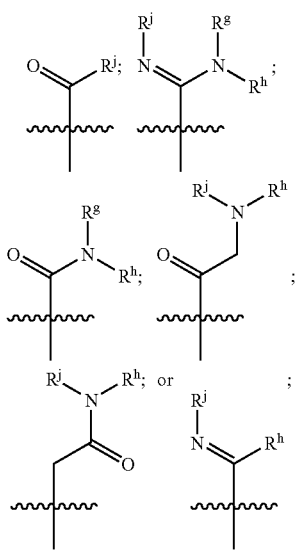

wherein $R^g$, $R^h$, $R^i$ and $R^j$ are hydrogen or alkyl.

In certain embodiments of the invention, the subject compounds may be of the formula II:

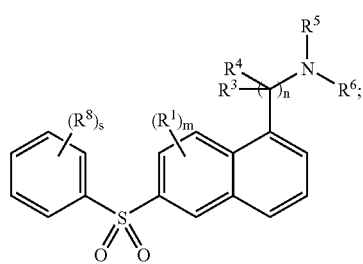

wherein:
s is from 0 to 4;
each $R^8$ is independently halo, alkyl, alkoxy, haloalkyl, heteroalkyl, cyano, —$S(O)_r$—$R^a$, —$C(=O)$—$NR^bR^c$, —$SO_2$—$NR^bR^c$, —$N(R^d)$—$C(=O)$—$R^e$, or —$C(=O)$—$R^e$, where r is from 0 to 2, $R^a$, $R^b$, $R^c$ and $R^d$ each independently is hydrogen or alkyl, and $R^e$ is hydrogen, alkyl, alkoxy or hydroxy; and
m, n, $R^1$, $R^3$, $R^4$, $R^5$ and $R^6$ are as defined herein.

In many embodiments of formula II, m is 0 or 1.
In certain embodiments of formula II, $R^1$ is halo.

In certain embodiments of formula II, m is 0 or 1 and $R^1$ is located at the 8-position of the naphthalene ring system.
In certain embodiments of formula II, n is 1.
In certain embodiments of formula II, n is 2.
In certain embodiments of formula II, n is 3.
In many embodiments of formula II, s is 0 or 1.
In many embodiments of formula II, m is 0 or 1 and $R^1$ is halo, preferably fluoro.
In many embodiments of formula II, s is 0 or 1 and $R^8$ is halo, preferably fluoro.
In many embodiments of formula II, s is 0 or 1 and $R^8$ is halo, alkyl, alkoxy or haloalkyl.
In certain embodiments of formula II, $R^3$ and $R^4$ are hydrogen.
In certain embodiments of formula II, one of $R^5$ and $R^6$ is hydrogen and the other is alkyl.
In certain embodiments of formula II, $R^5$ and $R^6$ are hydrogen.
In certain embodiments of formula II, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.
In certain embodiments of formula II, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.
In certain embodiments of formula II, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.
In certain embodiments of formula II, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.
In certain embodiments of formula II, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.
In certain embodiments of formula II, $R^5$ and $R^6$ together with the nitrogen to which they are attached form an amidinyl group.
In certain embodiments of formula II, $R^5$ and $R^6$ together with the nitrogen to which they are attached form a guanidinyl group.
In certain embodiments of formula II, $R^5$ and $R^6$ together with the nitrogen to which they are attached form a urea group.
In certain embodiments of formula II, $R^3$ and $R^4$ together with the nitrogen to which they are attached form =$NR^f$ wherein $R^f$ is hydrogen.
In certain embodiments of formula II, $R^3$ and $R^4$ together with the nitrogen to which they are attached form =O.
In certain embodiments of formula II, one of $R^5$ and $R^6$ and one of $R^3$ and $R^4$ together with the atoms to which they are attached form an imidazolinyl ring.
In certain embodiments of formula II, $R^5$ and $R^6$ together with the nitrogen to which they are attached form or a five- or six-membered heteroaryl ring that is optionally substituted and which optionally includes an additional nitrogen heteroatom.

In certain embodiments of formula II, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of formula II, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of formula II, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of formula II, one of $R^5$ and $R^6$ and one of $R^3$ and $R^4$ together with the atoms to which they are attached form an imidazolinyl ring.

In certain embodiments of formula II, s is from 0 to 2 and $R^7$ is halo, alkyl, alkoxy, haloalkyl, hydroxy, cyano or methanesulfonyl.

In certain embodiments of formula II, s is 0 or 1 and $R^7$ is halo.

In certain embodiments of formula II, m is 0 or 1, and n is 1.

In certain embodiments of formula II, m is 0 or 1, n is 1, and $R^3$ and $R^4$ are hydrogen.

In certain embodiments of formula II, m is 0 or 1, s is 0 or 1, $R^1$ and $R^8$ are halo, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula II, m is 0 or 1, n is 1, s is 0 or 1, $R^1$ and $R^8$ are halo, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula II, m is 0 or 1, s is 0 or 1, $R^1$ and $R^8$ are halo, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula II, m is 0 or 1, n is 1, s is 0 or 1, $R^1$ and $R^8$ are halo, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula II, m is 0 or 1, s is 0 or 1, $R^1$ and $R^8$ are halo, $R^3$ and $R^4$ are hydrogen, one of $R^5$ and $R^6$ is hydrogen and the other is alkyl.

In certain embodiments of formula II, m is 0 or 1, n is 1, s is 0 or 1, $R^1$ and $R^8$ are halo, $R^3$ and $R^4$ are hydrogen, one of $R^5$ and $R^6$ is hydrogen and the other is alkyl.

In certain embodiments of formula II, m is 0 or 1, s is 0 or 1, $R^1$ and $R^8$ are halo, $R^3$ and $R^4$ are hydrogen, one of $R^5$ and $R^6$ is hydrogen or alkyl, and the other is:

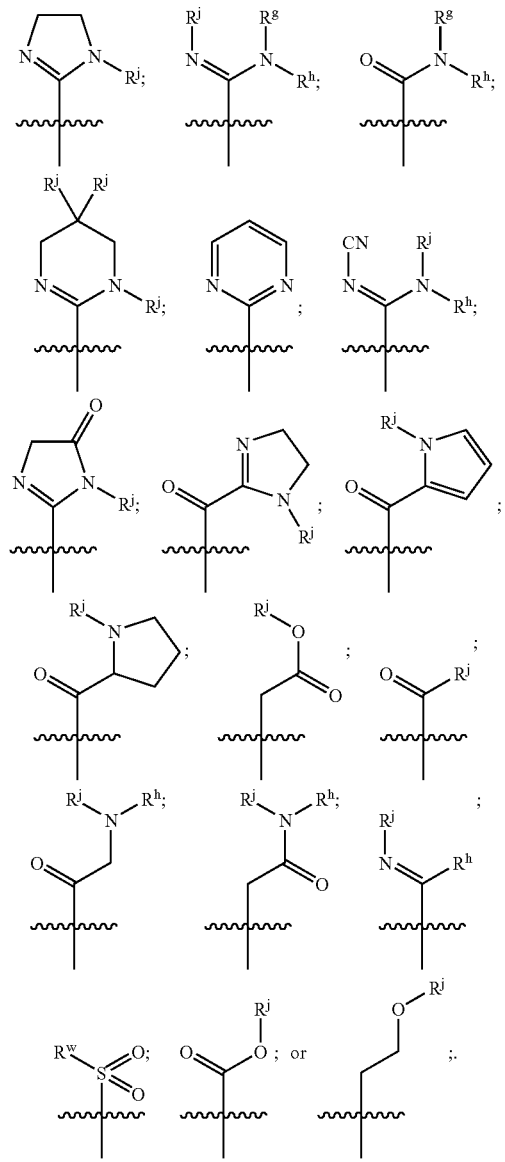

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^h R^i$.

In certain embodiments of formula II, m is 0 or 1, n is 1, s is 0 or 1, $R^1$ and $R^8$ are halo, $R^3$ and $R^4$ are hydrogen, one of $R^5$ and $R^6$ is hydrogen or alkyl, and the other is:

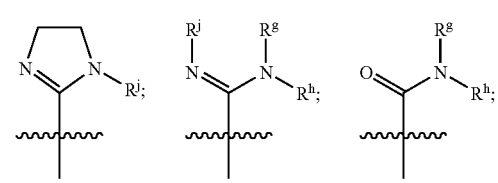

-continued

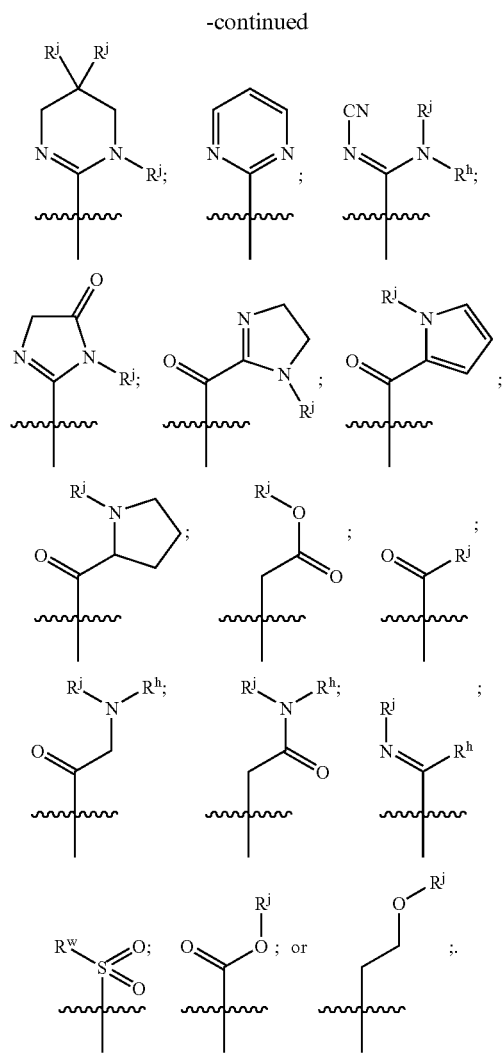

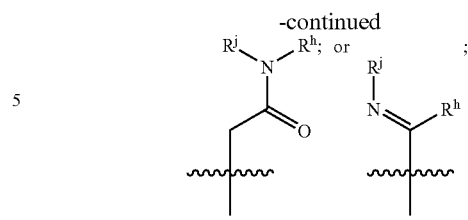

wherein $R^g$, $R^h$, $R^i$ and $R^j$ are hydrogen or alkyl.

In certain embodiments of formula II, m is 0 or 1, n is 1, s is 0 or 1, $R^1$ and $R^8$ are halo, $R^3$ and $R^4$ are hydrogen, one of $R^5$ and $R^6$ is hydrogen or alkyl, and the other is:

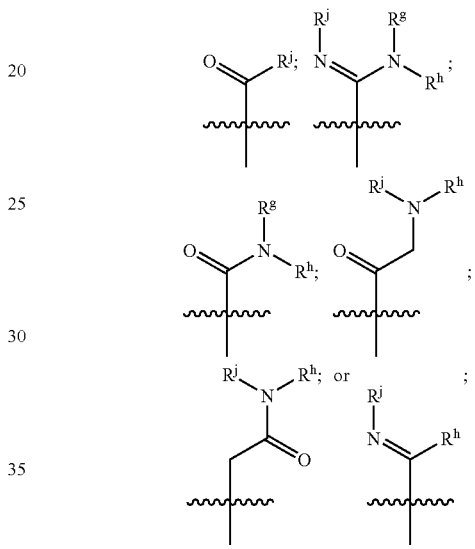

wherein $R^g$, $R^h$, $R^i$ and $R^j$ are hydrogen or alkyl.

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula II, m is 0 or 1, s is 0 or 1, $R^1$ and $R^8$ are halo, $R^3$ and $R^4$ are hydrogen, one of $R^5$ and $R^6$ is hydrogen or alkyl, and the other is:

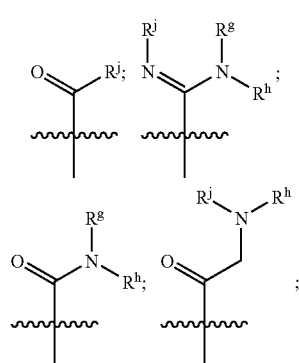

In certain embodiments of formula II, m is 0 or 1, s is 0 or 1, $R^1$ and $R^8$ are halo, and $R^3$ and $R^4$ together with the nitrogen to which they are attached form =$NR^f$ wherein $R^f$ is hydrogen, and wherein $R^5$ and $R^6$ are hydrogen.

In certain embodiments of formula II, m is 0 or 1, s is 0 or 1, $R^1$ and $R^8$ are halo, and $R^3$ and $R^4$ together with the nitrogen to which they are attached form =O.

In certain embodiments of formula II, m is 0 or 1, and n is 2.

In certain embodiments of formula II, m is 0 or 1, n is 2, and $R^3$ and $R^4$ are hydrogen.

In certain embodiments of formula II, m is 0 or 1, n is 2, s is 0 or 1, $R^1$ and $R^8$ are halo, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula II, m is 0 or 1, n is 2, s is 0 or 1, $R^1$ and $R^8$ are halo, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula II, m is 0 or 1, n is 2, s is 0 or 1, $R^1$ and $R^8$ are halo, $R^3$ and $R^4$ are hydrogen, one of $R^5$ and $R^6$ is hydrogen and the other is alkyl.

In certain embodiments of formula II, m is 0 or 1, n is 2, s is 0 or 1, $R^1$ and $R^8$ are halo, $R^3$ and $R^4$ are hydrogen, one of $R^5$ and $R^6$ is hydrogen or alkyl, and the other is:

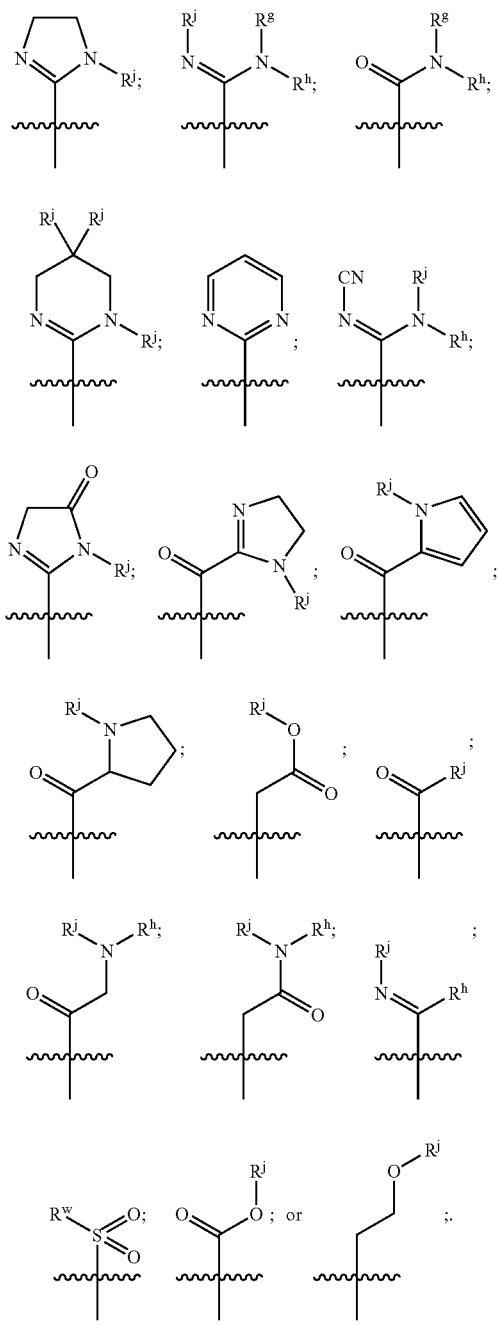

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula II, m is 0 or 1, n is 2, s is 0 or 1, $R^1$ and $R^8$ are halo, $R^3$ and $R^4$ are hydrogen, one of $R^5$ and $R^6$ is hydrogen or alkyl, and the other is:

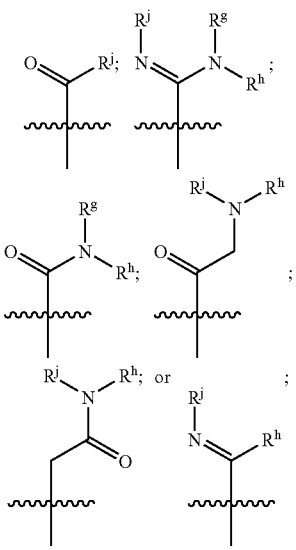

wherein $R^g$, $R^h$, $R^i$ and $R^j$ are hydrogen or alkyl.

In certain embodiments of formula II, m is 0 or 1, and n is 3.

In certain embodiments of formula II, m is 0 or 1, n is 1, and $R^3$ and $R^4$ are hydrogen.

In certain embodiments of formula II, m is 0 or 1, n is 3, s is 0 or 1, $R^1$ and $R^8$ are halo, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxyalkyl; or optionally substituted heteroaryl.

In certain embodiments of formula II, m is 0 or 1, n is 3, s is 0 or 1, $R^1$ and $R^8$ are halo, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula II, m is 0 or 1, n is 3, s is 0 or 1, $R^1$ and $R^8$ are halo, $R^3$ and $R^4$ are hydrogen, one of $R^5$ and $R^6$ is hydrogen or alkyl, and the other is:

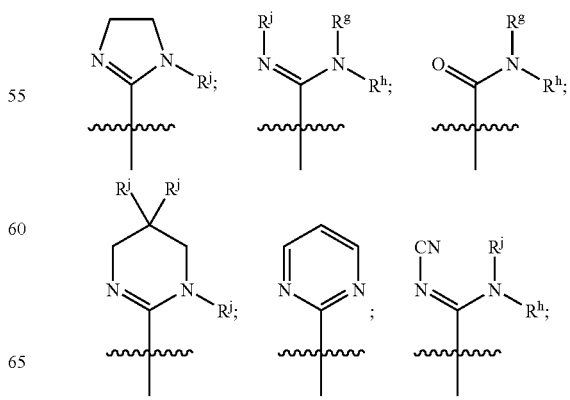

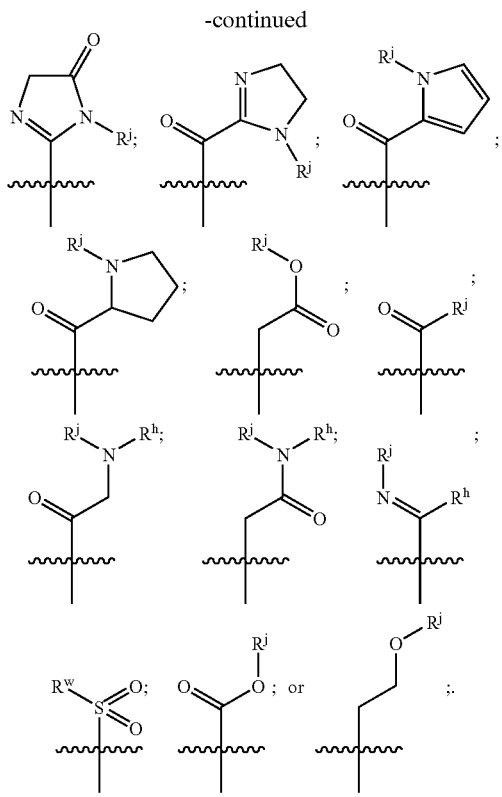

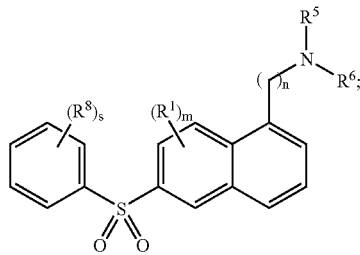
III wherein m, n, s, $R^1$, $R^5$, $R^6$ and $R^8$ are as defined herein.

In many embodiments of formula III, m is 0 or 1.

In certain embodiments of formula III, $R^1$ is halo.

In certain embodiments of formula III, m is 0 or 1 and $R^1$ is located at the 8-position of the naphthalene ring system.

In certain embodiments of formula III, n is 1.

In certain embodiments of formula III, n is 2.

In certain embodiments of formula III, n is 3.

In certain embodiments of formula III, one of $R^5$ and $R^6$ is hydrogen and the other is alkyl.

In certain embodiments of formula III, $R^5$ and $R^6$ are hydrogen.

In certain embodiments of formula III, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of formula III, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula III, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula III, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of formula III, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of formula III, $R^5$ and $R^6$ together with the nitrogen to which they are attached form an amidinyl group.

In certain embodiments of formula III, $R^5$ and $R^6$ together with the nitrogen to which they are attached form a guanidinyl group.

In certain embodiments of formula III, $R^5$ and $R^6$ together with the nitrogen to which they are attached form a urea group.

In certain embodiments of formula III, $R^5$ and $R^6$ together with the nitrogen to which they are attached form or a five- or wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula II, m is 0 or 1, n is 3, s is 0 or 1, $R^1$ and $R^8$ are halo, $R^3$ and $R^4$ are hydrogen, one of $R^5$ and $R^6$ is hydrogen or alkyl, and the other is:

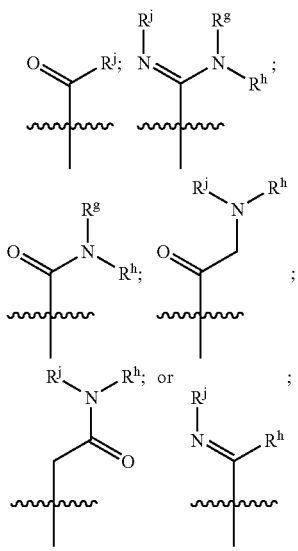

wherein $R^g$, $R^h$, $R^i$ and $R^j$ are hydrogen or alkyl

The subject compounds may, in certain embodiments, be more specifically of formula III:

six-membered heteroaryl ring that is optionally substituted and which optionally includes an additional nitrogen heteroatom.

In certain embodiments of formula III, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of formula III, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of formula III, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of formula III, one of $R^5$ and $R^6$ and one of $R^3$ and $R^4$ together with the atoms to which they are attached form an imidazolinyl ring.

In certain embodiments of formula III, s is from 0 to 2 and $R^8$ is halo, alkyl, alkoxy, haloalkyl, hydroxy, cyano or methanesulfonyl.

In certain embodiments of formula III, s is 0 or 1 and $R^8$ is halo.

In certain embodiments of formula III, and m is 0 or 1.

In certain embodiments of formula III, m is 0 or 1, and n is 1.

In certain embodiments of formula III, m is 0 or 1, s is 0 or 1, $R^1$ and $R^8$ are halo, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula III, m is 0 or 1, n is 1, s is 0 or 1, $R^1$ and $R^8$ are halo, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula III, m is 0 or 1, s is 0 or 1, $R^1$ and $R^8$ are halo, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula III, m is 0 or 1, n is 1, s is 0 or 1, $R^1$ and $R^8$ are halo, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula III, m is 0 or 1, s is 0 or 1, $R^1$ and $R^8$ are halo, one of $R^5$ and $R^6$ is hydrogen and the other is alkyl.

In certain embodiments of formula III, m is 0 or 1, n is 1, s is 0 or 1, $R^1$ and $R^8$ are halo, one of $R^5$ and $R^6$ is hydrogen and the other is alkyl.

In certain embodiments of formula III, m is 0 or 1, s is 0 or 1, $R^1$ and $R^8$ are halo, one of $R^5$ and $R^6$ is hydrogen or alkyl, and the other is:

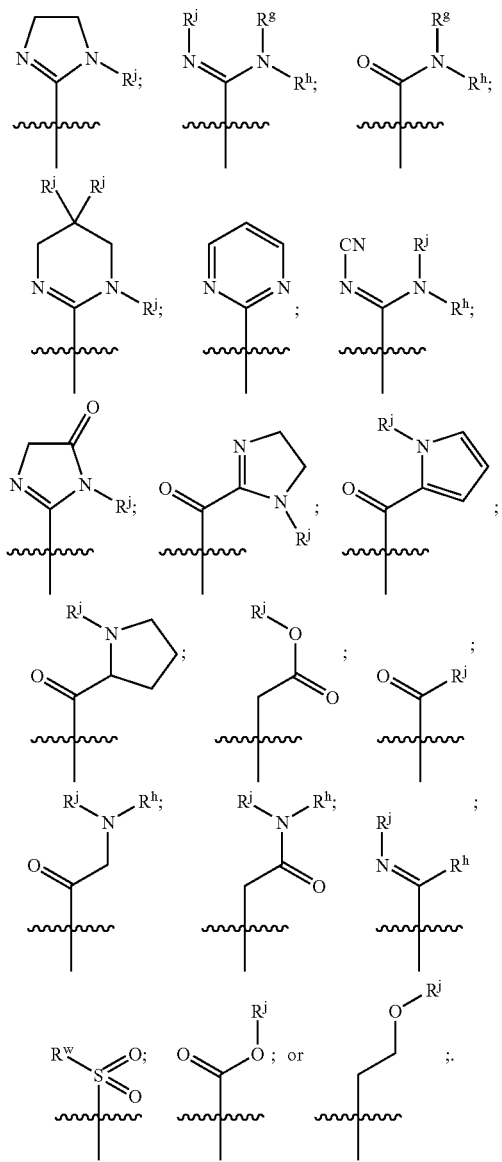

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or $—NR^hR^i$.

In certain embodiments of formula III, m is 0 or 1, n is 1, s is 0 or 1, $R^1$ and $R^8$ are halo, one of $R^5$ and $R^6$ is hydrogen or alkyl, and the other is:

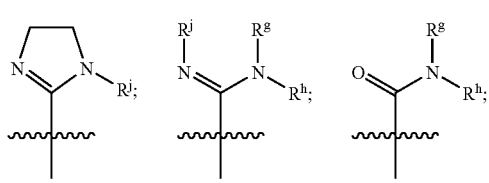

-continued

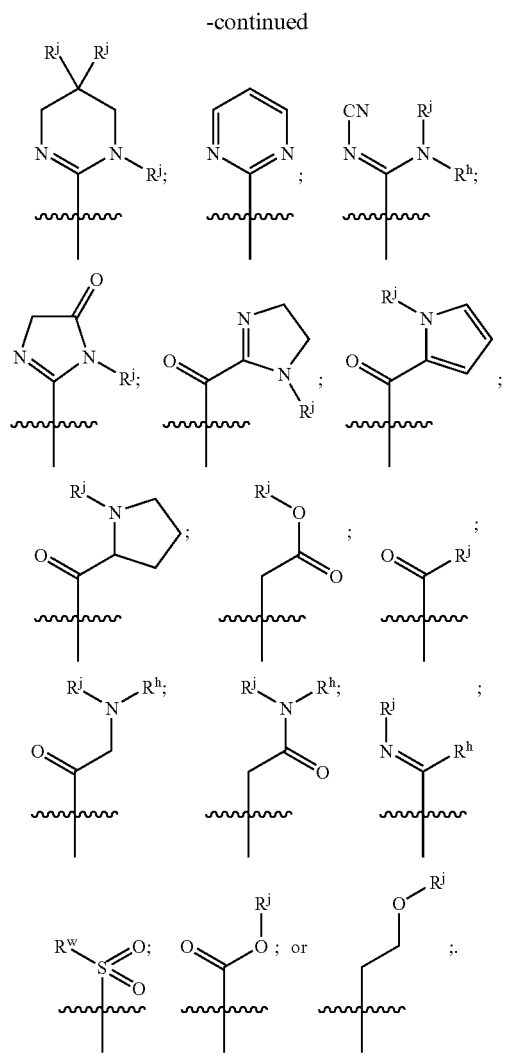

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula III, m is 0 or 1, s is 0 or 1, $R^1$ and $R^8$ are halo, one of $R^5$ and $R^6$ is hydrogen or alkyl, and the other is:

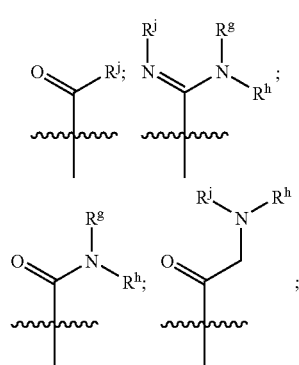

-continued

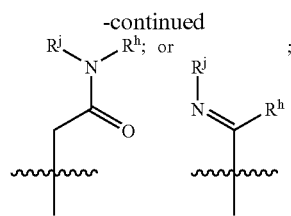

wherein $R^g$, $R^h$, $R^i$ and $R^j$ are hydrogen or alkyl.

In certain embodiments of formula III, m is 0 or 1, n is 1, s is 0 or 1, $R^1$ and $R^8$ are halo, one of $R^5$ and $R^6$ is hydrogen or alkyl, and the other is:

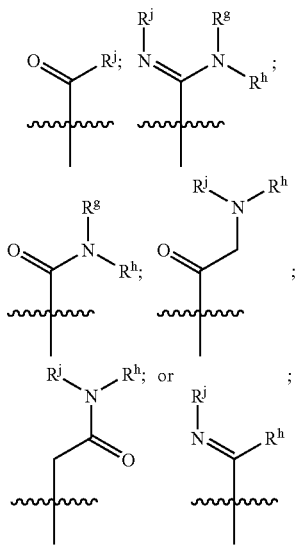

wherein $R^g$, $R^h$, $R^i$ and $R^j$ are hydrogen or alkyl.

In certain embodiments of formula III, m is 0 or 1, and n is 2.

In certain embodiments of either of formula IIIa or IIIb, m is 0 or 1, n is 2, s is 0 or 1, $R^1$ and $R^8$ are halo, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula III, m is 0 or 1, n is 2, s is 0 or 1, $R^1$ and $R^8$ are halo, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula III, m is 0 or 1, n is 2, s is 0 or 1, $R^1$ and $R^8$ are halo, one of $R^5$ and $R^6$ is hydrogen and the other is alkyl.

In certain embodiments of formula III, m is 0 or 1, n is 2, s is 0 or 1, $R^1$ and $R^8$ are halo, one of $R^5$ and $R^6$ is hydrogen or alkyl, and the other is:

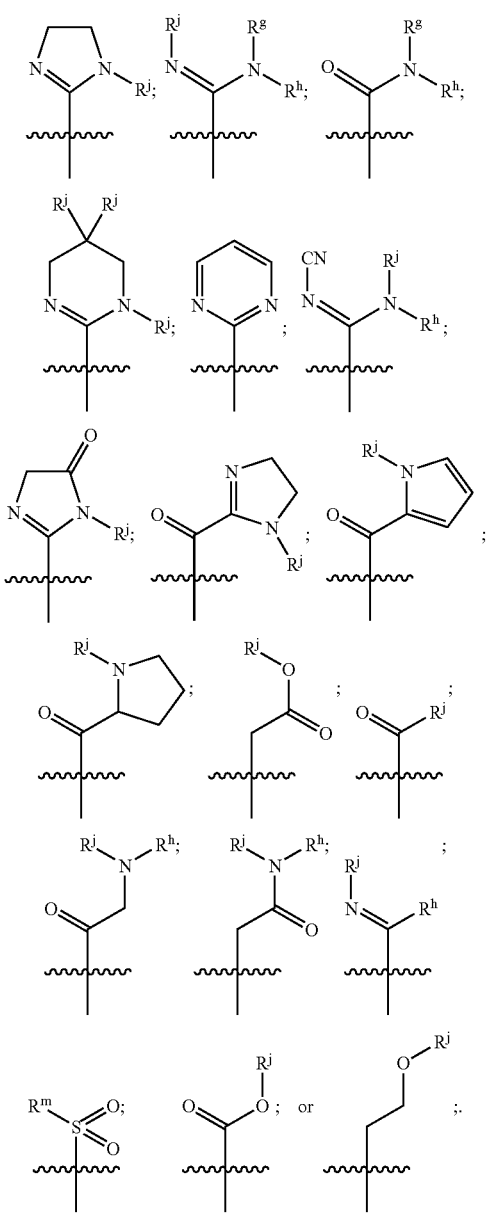

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula III, m is 0 or 1, n is 2, s is 0 or 1, $R^1$ and $R^8$ are halo, one of $R^5$ and $R^6$ is hydrogen or alkyl, and the other is:

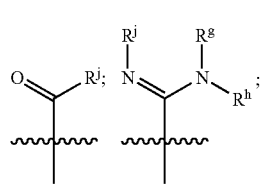

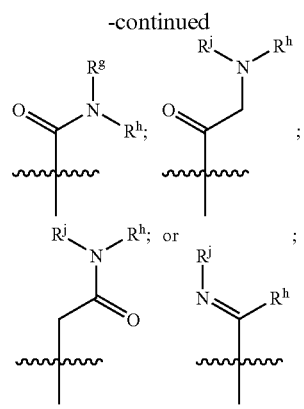

wherein $R^g$, $R^h$, $R^i$ and $R^j$ are hydrogen or alkyl.

In certain embodiments of formula III, m is 0 or 1, and n is 3.

In certain embodiments of formula III, m is 0 or 1, n is 3, s is 0 or 1, $R^1$ and $R^8$ are halo, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula III, m is 0 or 1, n is 3, s is 0 or 1, $R^1$ and $R^8$ are halo, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula III, m is 0 or 1, n is 3, s is 0 or 1, $R^1$ and $R^8$ are halo, one of $R^5$ and $R^6$ is hydrogen or alkyl, and the other is:

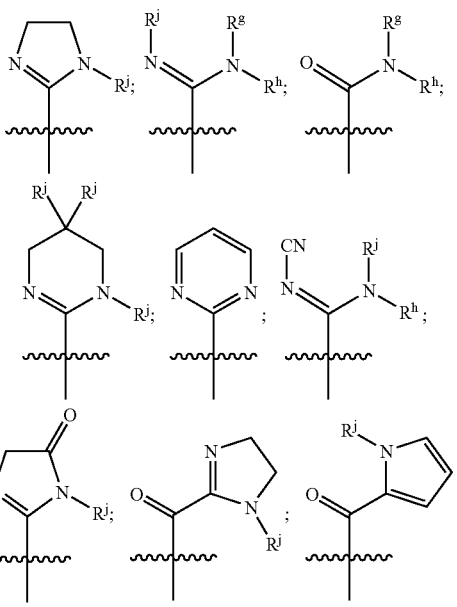

-continued

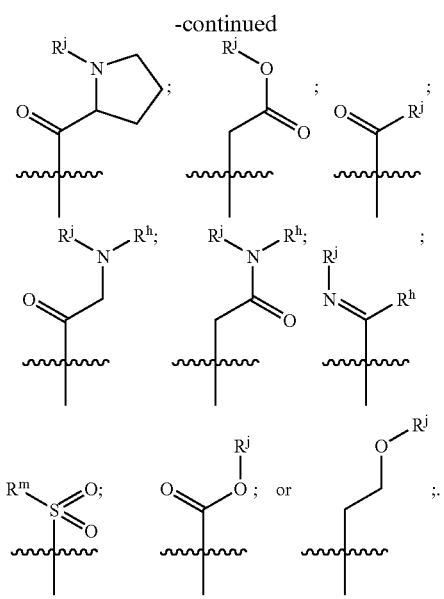

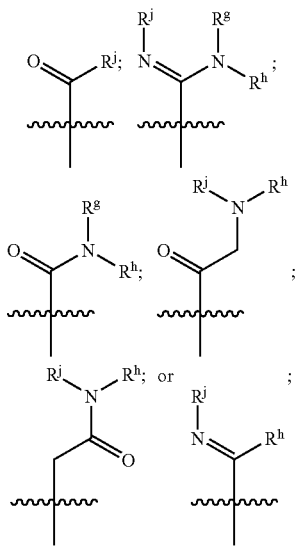

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula III, m is 0 or 1, n is 3, s is 0 or 1, $R^1$ and $R^8$ are halo, one of $R^5$ and $R^6$ is hydrogen or alkyl, and the other is:

wherein $R^g$, $R^h$, $R^i$ and $R^j$ are hydrogen or alkyl.

Where any of $R^1$, $R^2$, $R^3$, $R^4$, $R^5$, $R^6$, $R^7$, $R^8$, $R^a$, $R^b$, $R^c$, $R^d$, $R^e$, $R^f$, $R^g$, $R^h$, $R^i$, $R^j$, $R^k$, $R^m$ and $R^z$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the invention are shown in Table 1.

TABLE 1

| # | Structure | Name | M + H |
|---|-----------|------|-------|
| 1 | ![structure] | (6-Benzenesulfonyl-naphthalen-1-ylmethyl)-methyl-amine | 312 |
| 2 | ![structure] | C-[6-(3-Fluoro-benzenesulfonyl)-naphthalen-1-yl]-methylamine | 316 |
| 3 | ![structure] | N-[6-(3-Fluoro-benzenesulfonyl)-naphthalen-1-ylmethyl]-acetamide | 358 |

TABLE 1-continued

| # | Structure | Name | M + H |
|---|-----------|------|-------|
| 4 | 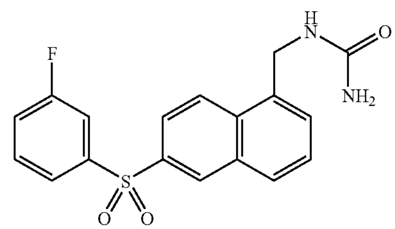 | [6-(3-Fluoro-benzenesulfonyl)-naphthalen-1-ylmethyl]-urea | 359 |
| 5 | 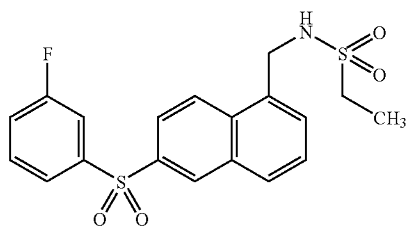 | Ethanesulfonic acid [6-(3-fluoro-benzenesulfonyl)-naphthalen-1-ylmethyl]-amide | 408 |
| 6 | 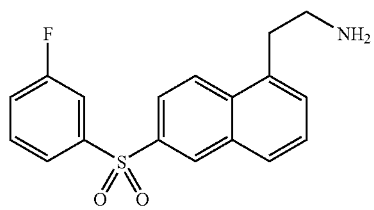 | 2-[6-(3-Fluoro-benzenesulfonyl)-naphthalen-1-yl]-ethylamine | 330 |
| 7 | 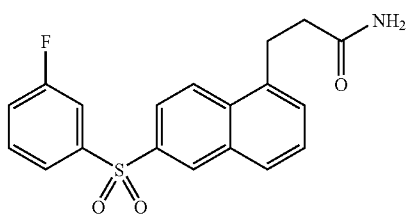 | 3-[6-(3-Fluoro-benzenesulfonyl)-naphthalen-1-yl]-propionamide | 358 |
| 8 | 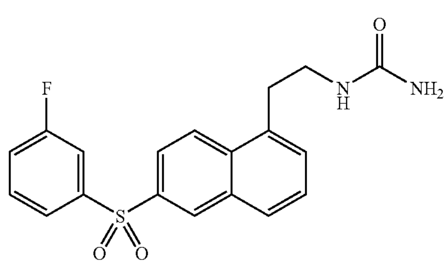 | {2-[6-(3-Fluoro-benzenesulfonyl)-naphthalen-1-yl]-ethyl}-urea | 373 |
| 9 | 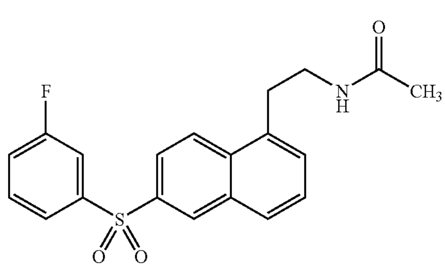 | N-{2-[6-(3-Fluoro-benzenesulfonyl)-naphthalen-1-yl]-ethyl}-acetamide | 372 |

TABLE 1-continued

| # | Structure | Name | M + H |
|---|---|---|---|
| 10 | 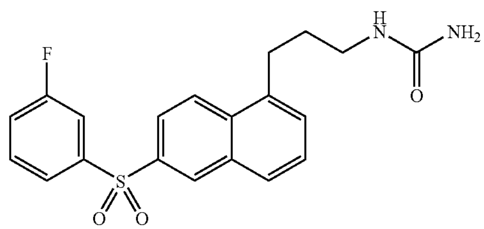 | {3-[6-(3-Fluoro-benzenesulfonyl)-naphthalen-1-yl]-propyl}-urea | 387 |
| 11 | 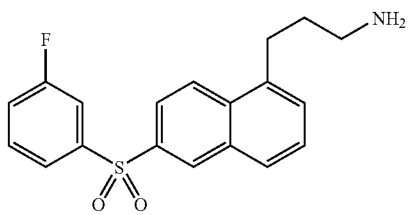 | 3-[6-(3-Fluoro-benzenesulfonyl)-naphthalen-1-yl]-propylamine | 344 |
| 12 | 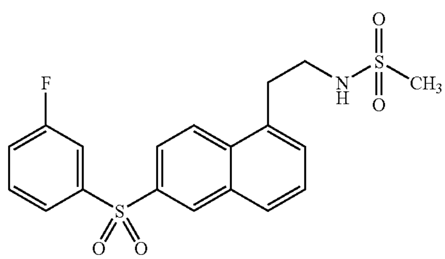 | N-{2-[6-(3-Fluoro-benzenesulfonyl)-naphthalen-1-yl]-ethyl}-methanesulfonamide | 408 |
| 13 | 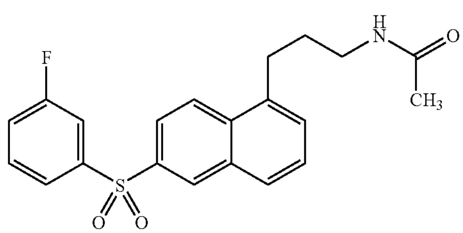 | N-{3-[6-(3-Fluoro-benzenesulfonyl)-naphthalen-1-yl]-propyl}-acetamide | 386 |
| 14 | 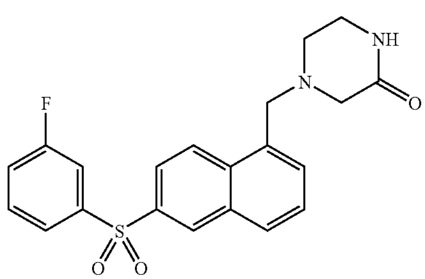 | 4-[6-(3-Fluoro-benzenesulfonyl)-naphthalen-1-ylmethyl]-piperazin-2-one | 399 |

Another aspect of the invention provides a composition comprising a therapeutically effective amount of at least one compound of formula (I) and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 2004, Volumes 1-56. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein Ar, m, q, $R^1$ and $R^7$ are as defined herein. Numerous synthetic routes to naphthalene compounds are known and may be used in preparation of the subject compounds, and the procedure of Scheme A is only exemplary. Specific examples of the procedure of Scheme A are provided in the following Experimental section.

SCHEME A

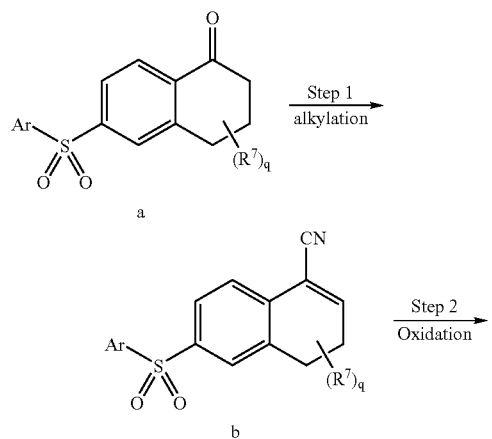

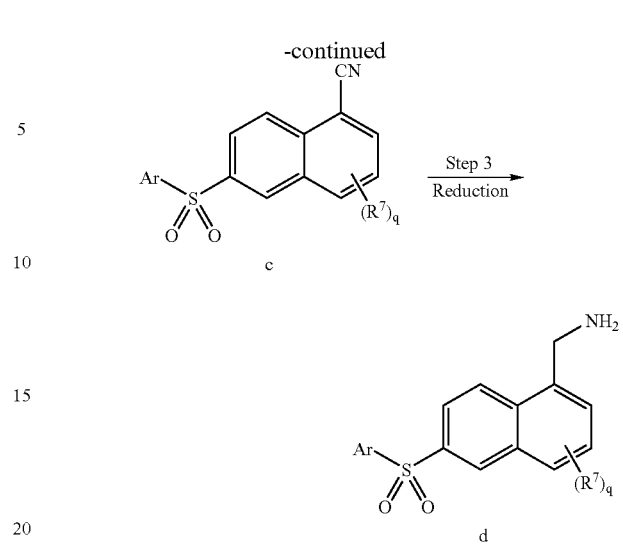

In step 1 of Scheme A, ketone compound a undergoes an alkylation/cyanylation reaction to give an arylsulfonyl nitrile compound b. Ketone compounds a may be prepared by a variety of techniques known in the art, and specific examples of preparing such compounds are provided below in the Experimental section of this disclosure. The alkylation reaction of step 1 may be achieved by treatment of ketone compound a with trimethylsilyl cyanide in the presence of zinc iodide under polar aprotic solvent conditions, followed by treatment with p-toluene sulfonic acid or like acid.

In step 2, arylsulfonyl nitrile compound b is subject to oxidation to provide arylsulfonyl naphthalene compound c. This oxidation may be achieved by treatment of compound b with dichloro-dicyano-benzoquinone.

A reduction reaction is carried out in step 3 to reduce the nitrile group of arylsulfonyl naphthalene compound c and afford an arylsulfonyl aminomethyl naphthalene compound d. Compound d is a compound of formula I in accordance with the invention.

The amine group of compound d of Scheme A may undergo various reactions to provide a variety of $R^2$ functional groups, as shown in Scheme B.

SCHEME B

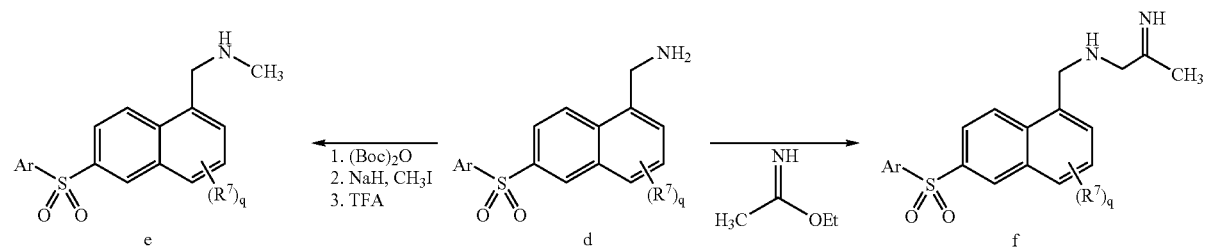

-continued

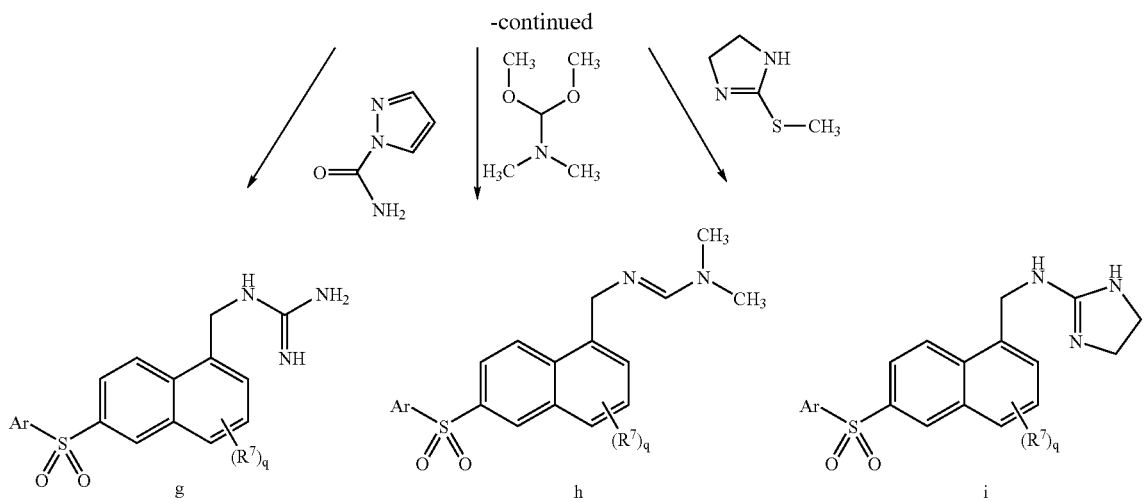

In Scheme B, compound d may be Boc protected, then subject to alkylation under reducing conditions, followed by deprotection to afford methylamino compound e. Compound e may be subject to another alkylation (not shown) to afford the corresponding dimethylamino or other dialkylamino compound.

Compound d may also be reacted with 1H-pyrazol-1-carboxamidine hydrochloride in the presence of amine catalyst under polar aprotic solvent conditions to afford guanidine compound g. Alternatively, compound d may be reacted with dimethylformamide dimethyl acetal to yield formamidine compound h. As yet another alternative, compound d may be treated with 2-methylsulfanyl-4,5-dihydro-1H-imidazole to afford imidazolinylamino compound i. In still another alternative, compound d may be reacted with ethyl imidate (acetimidic acid ethyl ester) to provide acetamidine compound f.

Many variations on the procedures of Scheme A and Scheme B are possible and will be readily apparent to those skilled in the art. Specific examples of such additional reactions are provided in the Examples below.

Utility

The compounds of the invention have selective affinity for 5-HT receptors, including the 5-HT$_6$ the 5-HT$_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

Abbreviations

DCM dichloromethane/methylene chloride
DDQ 2,3-dichloro-5,6-dicyano-1,4-benzoquinone
Dibal diisobutyl aluminum hydride
DMF N,N-dimethylformamide
DMAP 4-dimethylaminopyridine
EtOAc ethyl acetate
EtOH ethanol
tBuOH tert-butanol
gc gas chromatography
HMPA hexamethylphosphoramide
hplc high performance liquid chromatography
mCPBA m-chloroperbenzoic acid
MeCN acetonitrile
NMP N-methyl pyrrolidinone
TEA triethylamine
TFA trifluoroacetic acid
THF tetrahydrofuran
LDA lithium diisopropylamine
TLC thin layer chromatography Additional procedures for making compounds of the invention are found in U.S. patent application Ser. No. 11/315,706, filed on Dec. 21, 2005, the disclosure of which is incorporated herein by reference.

Preparation 1

6-Benzenesulfonyl-3,4-dihydro-2H-naphthalen-1-one

The synthetic procedure described in this Preparation was carried out according to the process shown in Scheme C.

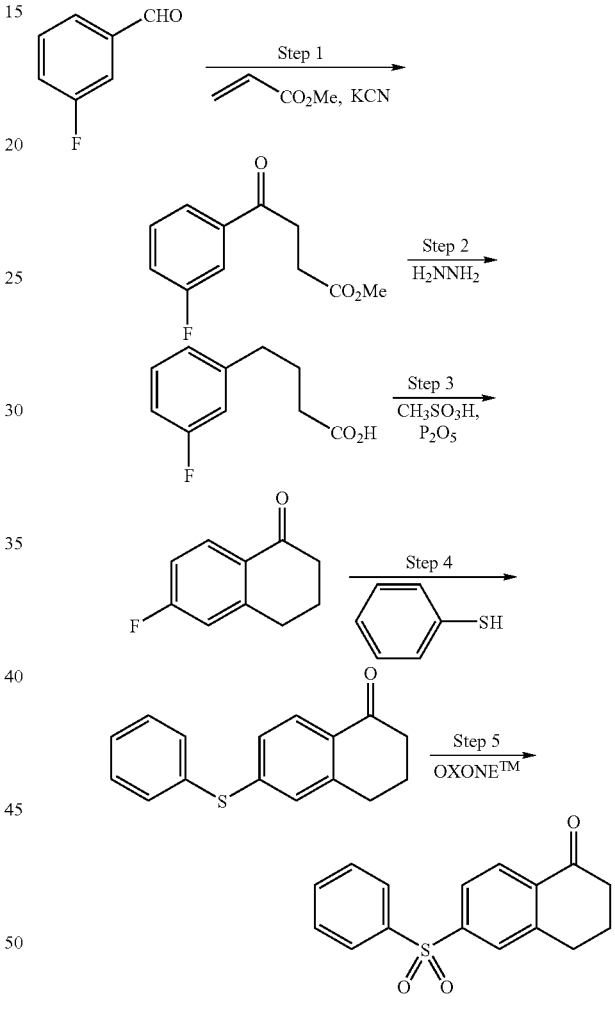

Step 1 4-(3-Fluoro-phenyl)-4-oxo-butyric acid methyl ester

A solution of 3-fluorobenzaldehyde (35.38 g, 285.07 mmol) in 35 mL dimethylformamide (DMF) was added to a heated (48° C.) solution of methyl acrylate (26.28 mL, 25.03 g, 290.7 mmol) and powdered KCN under Argon. The reaction mixture was stirred at 40° C. for 2 hours and then poured into 500 mL of water. This aqueous phase was extracted twice with 500 mL of Et$_2$O and once with 250 mL of EtOAc. The combined organic layers were washed with water and saturated brine, and then dried over MgSO$_4$. The solvent was evaporated under reduced pressure to give 50.89 g (242.2 mmol, 84.93%) of 4-(3-fluoro-phenyl)-4-oxo-butyric acid methyl ester as an oil. MS: 211 (M+H)$^+$.

Step 2 4-(3-Fluoro-phenyl)-butyric acid

A solution of 4-(3-fluoro-phenyl)-4-oxo-butyric acid methyl ester (28.27 g, 134.49 mmol), hydrazine monohydrate (26.1 mL, 26.93 g, 537.96 mmol) and KOH (22.64 g, 403.47 mmol) in ethylene glycol (150 mL) was heated to reflux under argon and refluxed for 2 hours. The reaction mixture was cooled and diluted with 1.5 litres of water, 500 mL of $Et_2O$ was added, and the mixtures was acidified by addition of 6 M HCl with stirring, after which an additional 500 mL of $Et_2O$ was added. The organic layer was removed and the aqueous layer was extracted twice with 250 mL of 500 mL of $Et_2O$/ EtOAc (3:1). The combined organic layers were washed with water, saturated brine, and then dried over $MgSO_4$. The solvent was evaporated under reduced pressure to yield a brownish oil, which was eluted through silica gel using hexanes/ EtOAc (9:1). Removal of solvent under reduced pressure yielded 18.44 g (101.21 mmol, 75.26%) of 4-(3-fluoro-phenyl)-butyric acid as an oil. MS: 183 (M+H)$^+$.

Step 3 6-Fluoro-3,4-dihydro-2H-naphthalen-1-one

A solution of methanesulfonic acid (75 mL) and $P_2O_5$ was stirred at 85° C. for 15 minutes, at which point most of the $P_2O_5$ had dissolved. An additional 15 mL of methanesulfonic acid was added dropwise, and the mixture was stirred at 85° C. for 2 hours. The reaction mixture was poured into 500 mL of water and extracted twice with 400 mL of EtOAc. The combined organic layers were washed with saturated $NaHCO_3$, water, and saturated brine, and then dried over $MgSO_4$. The solvent was removed under reduced pressure to give an oil that was eluted through silica gel using hexanes/ EtOAc (9:1). Removal of solvent under reduced pressure yielded 6.06 g, 36.91 mmol, 53.97%) of 6-fluoro-3,4-dihydro-2H-naphthalen-1-one as a yellow oil. MS: 165 (M+H)$^+$.

Step 4
6-Phenylsulfanyl-3,4-dihydro-2H-naphthalen-1-one

A solution of 6-fluoro-3,4-dihydro-2H-naphthalen-1-one (5.51 g, 33.56 mmol), benzenethiol (4.07 g, 3.79 mL, 36.92 mmol) and $K_2CO_3$ (9.28 g, 67.12 mmol) in 50 mL of N-methylpyrrolidinone (NMP) was heated to 80° C. under argon and stirred at 80° C. for 2 hours. The reaction mixture was poured into 500 mL of water and diluted with 300 mL of EtOAc. The layers were separated and the aqueous layer was extracted twice with 250 mL of EtOAc. The combined organic layers were washed with water, saturated brine, and then dried over $MgSO_4$. The solvent was removed under reduced pressure to yield an oil which was eluted through silica gel using hexanes/EtOAc (9:1). Removal of solvent under reduced pressure provided 8.05 g (31.65 mmol, 94.31%) of 6-phenylsulfanyl-3,4-dihydro-2H-naphthalen-1-one as a pale yellow oil. MS: 255 (M+H)$^+$.

Step 5
6-Benzenesulfonyl-3,4-dihydro-2H-naphthalen-1-one

A solution of 6-phenylsulfanyl-3,4-dihydro-2H-naphthalen-1-one (8.05 g, 31.65 mmol) in MeOH/MeCN (50 mL of each) was stirred at room temperature. OXONE™ (potassium peroxymonosulfate, 77.83 g, 126.60 mmol) was dissolved in 50 mL of water and was added to the stirring reaction. The reaction mixture was stirred for 15 hours, and then evaporated under reduced pressure. The resulting aqueous residue was diluted with 500 mL of water and extracted three times with 300 mL of EtOAc. The combined extracts were washed with water, saturated brine, and dried over $MgSO_4$. The solvent was removed under reduced pressure to yield an oil which was eluted through silica gel with hexane followed by chloroform. Removal of solvent under reduced pressure afforded 6.55 g (22.87 mmol, 72.27%) of a white solid, which was recrystallized from $EtO_2$/hexanes. MS: 287 (M+H)$^+$.

Similarly prepared using the above procedure with 3-fluoro-benzenethiol in step 4, was 6-(3-fluoro-benzenesulfonyl)-3,4-dihydro-2H-naphthalen-1-one. MS: 305 (M+H)$^+$.

Preparation 2

7-Benzenesulfonyl-3,4-dihydro-2H-naphthalen-1-one

The synthetic procedure described in this Preparation was carried out according to the process shown in Scheme D.

SCHEME D

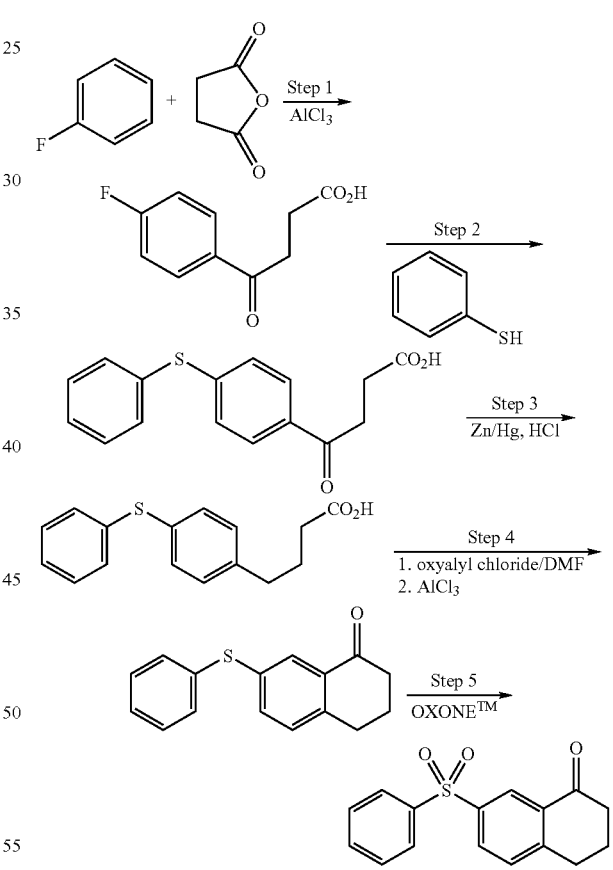

Step 1: 4-(4-Fluoro-phenyl)-4-oxo-butyric acid

Fluorobenzene (50 mL, 530 mmol) and aluminum trichloride (156 g, 1.17 mol) were added to 500 mL of methylene chloride, and the reaction mixture was stirred. Succinic anhydride (50 g, 500 mmol) was added to the stirring reaction mixture all at once, and the reaction mixture was stirred at room temperature for 2 hours. The reaction was quenched by cautious addition of 10% HCl, and the reaction mixture was added to 500 mL of water. The aqueous mixture was extracted twice with 250 mL of methylene chloride, and the combined organic layers were dried (MgSO$_4$), and evaporated under reduced pressure to give 62 g (316 mmol, 59.6%) of 4-(4-fluoro-phenyl)-4-oxo-butyric acid as a crude solid. MS: 197 (M+H)$^+$.

Step 2: 4-Oxo-4-(4-phenylsulfanyl-phenyl)-butyric acid 4-(4-Fluoro-phenyl)-4-oxo-butyric acid (10.0 g, 51 mmol), thiophenol (5.2 g, 51 mmol) and powdered potassium carbonate (13.8 g, 100 mmol) were added to 25 mL of dimethyl sulfoxide (DMSO). The reaction mixture was heated to 110° C. for 2 hours, then cooled and diluted by addition of 250 mL water. The aqueous mixture was extracted three times with 100 mL of EtOAc, and the combined organic layers were dried (MgSO$_4$), and evaporated under reduced pressure to yield 11 g (38.5 mmol, 75.5%) of 4-oxo-4-(4-phenylsulfanyl-phenyl)-butyric acid as a crude solid. MS: 287 (M+H)$^+$.

Step 3: 4-(4-Phenylsulfanyl-phenyl)-butyric acid

Powdered Zinc (66 g) was washed with 2% HCl, added to a solution of HgCl$_2$ (6 g) in 50 mL of 6M HCl. This mixture was shaken vigorously for 5 minutes, and excess liquid was decanted. The mixture was then added to a mechanically stirred suspension of 4-oxo-4-(4-phenylsulfanyl-phenyl)-butyric acid (6.5 g, 22.7 mmol) in 450 mL of 6M HCl, and the reaction mixture was stirred at room temperature for 5 days. The mixture was then decanted to remove excess HCl, and quenched by addition of 250 mL water. The aqueous mixture was extracted three times with 100 mL of EtOAc, and the combined organic layers were dried under reduced pressure to yield 5.0 g (18.4 mmol, 81%) of 4-(4-phenylsulfanyl-phenyl)-butyric acid as a crude solid. MS: 273 (M+H)$^+$.

Step 4: 7-Phenylsulfanyl-3,4-dihydro-2H-naphthalen-1-one 4-(4-Phenylsulfanyl-phenyl)-butyric acid (5.0 g, 18.4 mmol) was dissolved in 50 mL tetrahydrofuran (THF). Oxalyl chloride (1.8 mL, 20 mmol) and one drop of DMF were added, and the reaction mixture was stirred for 1 hour, and then evaporated to dryness under reduced pressure. The resulting residue was dissolved in 40 mL of 1,2-dichloroethane, and aluminum trichloride (0.85 g, 25 mmol) was added all at once. The reaction mixture was stirred for 1 hour, and quenched by addition of 2% HCl. This aqueous mixture was extracted twice with 100 mL of EtOAc, and the combined organic layers were dried (MgSO$_4$) and evaporated to yield 2.54 g (10 mmol, 55.5%) of 7-phenylsulfanyl-3,4-dihydro-2H-naphthalen-1-one as a gummy residue. MS: 255 (M+H)$^+$.

Step 5: 7-Benzenesulfonyl-3,4-dihydro-2H-naphthalen-1-one

7-Phenylsulfanyl-3,4-dihydro-2H-naphthalen-1-one ( ) was dissolved in 50 mL of MeOH and stirred at room temperature. OXONE™ (13.5 g, 22 mmol) was dissolved in 10 mL of water and added to the stirring reaction. The reaction mixture was stirred for 8 hours, and then evaporated under reduced pressure. The resulting aqueous residue was diluted with 200 mL of water and extracted three times with 100 mL of EtOAc. The combined extracts were dried over MgSO$_4$, and the solvent was removed under reduced pressure to yield an oil which was eluted through silica gel with 1:1 EtOAc/hexanes. Removal of solvent under reduced pressure afforded 1.7 g (5.9 mmol, 59%) of 7-benzenesulfonyl-3,4-dihydro-2H-naphthalen-1-one as an oil. MS: 287 (M+H)$^+$.

Similarly prepared using the above procedure with 4-fluorobenzenethiol in step 2, was 7-(4-fluoro-benzenesulfonyl)-3,4-dihydro-2H-naphthalen-1-one. MS: 287 (M+H)$^+$.

Example 1

(6-Benzenesulfonyl-naphthalen-1-ylmethyl)-methyl-amine

The synthetic procedure described in this Example was carried out according to the process shown in Scheme F.

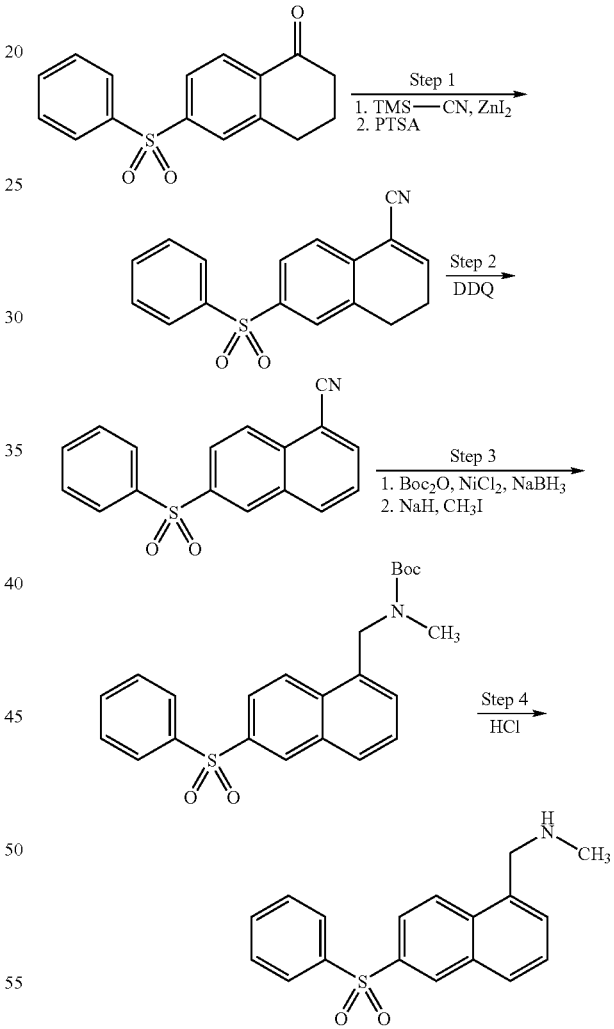

SCHEME F

Step 1 6-Benzenesulfonyl-3,4-dihydro-naphthalene-1-carbonitrile

6-Benzenesulfonyl-3,4-dihydro-2H-naphthalen-1-one from Preparation 1 above (4.0 g, 14 mmol), trimethylsilyl cyanide (10.0 g, 100 mmol) and Zinc Iodide (0.25 g) were combined and stirred under nitrogen for 15 hours. The reaction mixture was then diluted by addition of 200 mL of Et$_2$O, washed with cold water, and the organic layer was dried (MgSO$_4$) and evaporated under reduced pressure to an oil. The oil was dissolved in 250 mL of toluene, and 0.5 g of paratoluene sulfonic acid was added. The reaction mixture was refluxed for three hours, cooled, and the solvent was removed under reduced pressure. The crude product was eluted through silica under medium pressure with 5% EtOAc in hexanes to yield 1.8 g (6.1 mmol, 44%) of (racemic) 6-benzenesulfonyl-3,4-dihydro-naphthalene-1-carbonitrile as an oil. MS: 296 (M+H)$^+$.

Step 2 6-Benzenesulfonyl-naphthalene-1-carbonitrile

A mixture of 0.89 g (3 mmoles) 6-benzenesulfonyl-3,4-dihydro-naphthalene-1-carbonitrile and 0.68 g (3 mmoles) DDQ in 15 mL dioxane was heated under reflux for 18 hours. Another 0.25 g (0.12 mmole) DDQ was added and the reaction mixture was heated under reflux for another 20 hours. The mixture was filtered and the collected solids were washed with diethyl ether. The filtrate was concentrated under reduced pressure and the residue was dissolved in ethyl acetate and washed with 5% sodium hydroxide and half-saturated aqueous sodium chloride. The organic phase was dried (magnesium sulfate) and concentrated under reduced pressure. The residue was subjected to column chromatography over silica gel 230-400 mesh eluting with chloroform: hexane:ethyl acetate (50:49:1), then with 50:48:2 and finally with 50:46:4. The title compound was obtained as a white solid, 0.266 gram (30%). NMR (CDCl$_3$) ppm δ: 8.67 (d, 1H, J=1.8 Hz), 8.34 (d, 1H, J=8.8 Hz), 8.24 (d, 1H, J=8.41 Hz), 8.04 (m, 4H), 7.69 (dd, 1H, J=4.25 Hz, J=11.5 Hz), 7.56 (m 3H).

Step 3 (6-Benzenesulfonyl-naphthalen-1-ylmethyl)-methyl-carbamic acid tert-butyl ester A mixture of 0.26 gram (0.89 mmole) 6-benzenesulfonyl-naphthalene-1-carbonitrile, 0.39 g (1.8 mmole) di-tert-butyl dicarbonate and 0.022 g (0.092 mmole) nickel chloride hexahydrate in 8 mL methanol was cooled to 0° C. Solid sodium borohydride (0.235 g, 6.2 mmole) was added in portions over 35 minutes. The reaction mixture was stirred at 23° C. for two hours. To the mixture was added 3 drops of diethylenetriamine. The mixture was stirred at 23° C. for 30 minutes, then was concentrated under reduced pressure. The residue was partitioned between ethyl acetate and saturated sodium bicarbonate. The organic phase was dried (magnesium sulfate) and concentrated under reduced pressure. The resulting crude (6-benzenesulfonyl-naphthalen-1-ylmethyl)-carbamic acid tert-butyl ester was dissolved in 3 mL THF and added dropwise to a mixture of 0.043 g (1.07 mmole) 60% sodium hydride and 0.13 mL (0.92 mmole) iodomethane in 3 mL THF. The reaction mixture was stirred at 23° C. for 18 hours, then another 0.025 g 60% sodium hydride and 5 drops iodomethane were added. The mixture was stirred for an additional 20 hours, then another 0.03 g of 60% sodium hydride and 6 drops iodomethane were added. After stirring for an additional 3 days, the mixture was diluted with 10 mL diethyl ether and washed with water. The organic phase was dried (magnesium sulfate) and concentrated under reduced pressure. The residue was subjected to column chromatography over silica gel 230-400 mesh eluting with a gradient of 2-50% ethyl acetate in hexane. The title compound was obtained as a colorless foam, 0.25 gram (68%). NMR (CDCl$_3$) ppm δ: 8.67 (d, 1H, J=1.82 Hz), 8.27, (br s, 1H), 8.01 (dd, 2H, J=1.36 Hz, J=4.51 Hz), 7.91 (m, 3H), 7.52 (m, 5H), 4.88 (s, 2H), 2.73 (br s, 3H), 1.49 (s, 9H).

Step 4 (6-Benzenesulfonyl-naphthalen-1-ylmethyl)-methyl-amine

A solution of 0.245 g (0.6 mmoles) (6-benzenesulfonyl-naphthalen-1-ylmethyl)-methyl-carbamic acid tert-butyl ester and 20 mL 2 M hydrogen chloride in ethyl ether was stirred at 23° C. for 20 hours. The resulting white solid was collected by filtration and dried in vacuo to provide (6-benzenesulfonyl-naphthalen-1-ylmethyl)-methyl-amine as a hydrochloride salt, 0.12 gram (57%), M$^+$H=312.

Example 2

C-(6-Benzenesulfonyl-naphthalen-1-yl)-methylamine

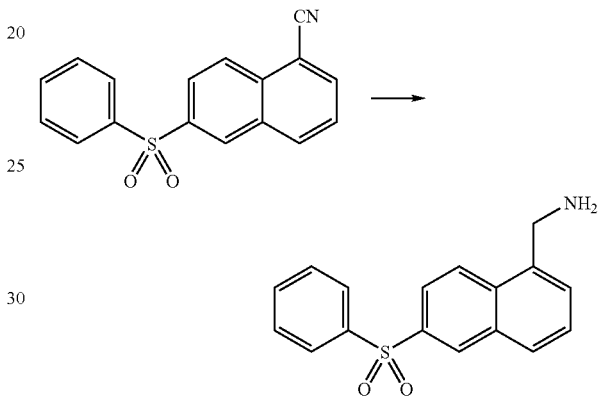

6-Benzenesulfonyl-naphthalene-1-carbonitrile is dissolved in dry THF and cooled to ice bath temperature. Borane-THF complex is added and the reaction mixture is stirred under nitrogen overnight at room temperature. The reaction is quenched by addition of HCl and methanol, and made basic by addition of 1M NaOH. The resulting residue is extracted with EtOAc, and the organic layer is dried (MgSO$_4$), filtered and concentrated under reduced pressure. The residue is recrystallized from HCl/EtOH to give C-(6-Benzenesulfonyl-naphthalen-1-yl)-methylamine as a hydrochloride salt.

Example 3

2-[6-(3-Fluoro-benzenesulfonyl)-naphthalen-1-yl]-ethylamine

The synthetic procedure described in this Example was carried out according to the process shown in Scheme G.

SCHEME G

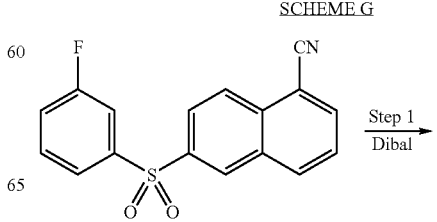

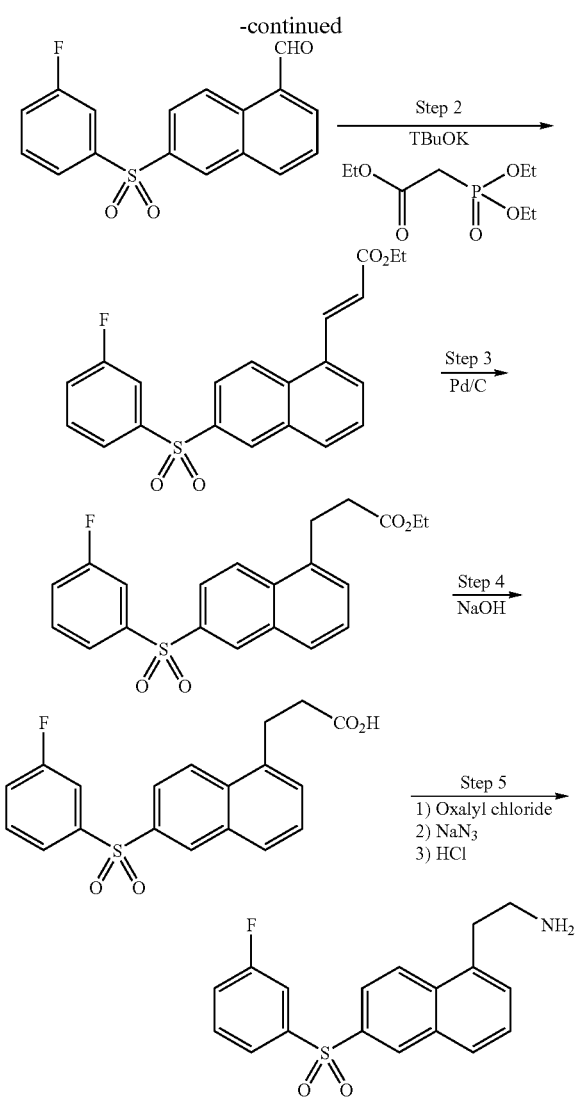

Step 1 6-(3-Fluoro-benzenesulfonyl)-naphthalene-1-carbaldehyde

Dibal (11 mL of 1.5 M Toluene suspension) was added dropwise to a stirring room temperature solution of 6-benzenesulfonyl-3,4-dihydro-naphthalene-1-carbonitrile (4.5 g, 14.5 mmol) in 100 mL toluene. The reaction mixture was stirred for four hours at room temperature, then quenched by addition of 10% aqueous HCl (25 mL). The mixture was diluted with brine, extracted once with THF, extracted once with a 1:1 mixture of EtOAc/THF, and the combined organic layers were dried over MgSO$_4$, filtered, and concentrated under reduced pressure. The residue was eluted through silica gel with methylene chloride as solvent. The combined fractions were triturated with methyl tert-butyl ether, and the resulting precipitate was collected by filtration and dried to give 2.55 g of 6-(3-fluoro-benzenesulfonyl)-naphthalene-1-carbaldehyde.

Step 2 3-[6-(3-Fluoro-benzenesulfonyl)-naphthalen-1-yl]-acrylic acid ethyl ester Potassium tert-butoxide (6.5 mL of 1M THF solution) was added dropwise to 1.3 mL of triethylphosphonyl acetate (6.5 mmol) at 0° C. This solution was then added dropwise to a room temperature solution of 6-(3-Fluoro-benzenesulfonyl)-naphthalene-1-carbaldehyde (1.7 g, 5.4 mmol) in 100 mL THF. The reaction mixture was stirred for 18 hours at room temperature, then quenched with dilute aqueous HCl. The mixture was extracted with EtOAc, and the combined organic layers were washed with brine, dried over MgSO$_4$, filtered, and concentrated under reduced pressure to give 2.1 g of crude 3-[6-(3-fluoro-benzenesulfonyl)-naphthalen-1-yl]-acrylic acid ethyl ester, which was used directly without further purification.

Step 3 3-[6-(3-Fluoro-benzenesulfonyl)-naphthalen-1-yl]-propionic acid ethyl ester 3-[6-(3-Fluoro-benzenesulfonyl)-naphthalen-1-yl]-acrylic acid ethyl ester (2.0 g) was dissolved in a mixture of methanol (20 mL), acetic acid (20 mL) and EtOAc (50 mL) in a Parr vessel. Palladium on activated carbon (1.0 g, 10% Pd) was added, and the vessel was purged with nitrogen. The reaction mixture was stirred at room temperature under 60 atm (4.14 Bar) hydrogen for 18 hours. The vessel was purged with nitrogen, and the reaction mixture was removed and filtered through Celite. The filtrate was evaporated under reduced pressure to give 2.0 g of 3-[6-(3-fluoro-benzenesulfonyl)-naphthalen-1-yl]-propionic acid ethyl ester.

Step 4 3-[6-(3-Fluoro-benzenesulfonyl)-naphthalen-1-yl]-propionic acid

3-[6-(3-Fluoro-benzenesulfonyl)-naphthalen-1-yl]-propionic acid ethyl ester (2.0 g) was dissolved in 25 mL ethanol, and 10 mL of 25% aqueous NaOH was added. The reaction mixture was heated to reflux for one hour, then cooled to room temperature. The ethanol was removed under reduced pressure, and the liquid residue was acidified by addition of 10% aqueous HCl. The mixture was extracted with EtOAc, and the combined organic layers were dried over MgSO$_4$, filtered, and concentrated under reduced pressure to give a crude oil. The oil was dissolved in warm toluene and insolubles were removed by filtration. The filtrate was concentrated under reduced pressure to give 1.6 g of 3-[6-(3-fluoro-benzenesulfonyl)-naphthalen-1-yl]-propionic acid.

Step 5 2-[6-(3-Fluoro-benzenesulfonyl)-naphthalen-1-yl]-ethylamine

To a suspension of 3-[6-(3-Fluoro-benzenesulfonyl)-naphthalen-1-yl]-propionic acid (1.0 g, 2.8 mmol) in 35 mL methylene chloride was added 0.8 mL oxalyl chloride. One drop of DMF was added, and the reaction mixture was stirred for 10 minutes at room temperature. The reaction mixture was concentrated under reduced pressure, and the resulting residue was dissolved in 25 mL acetone and cooled in an ice bath. A solution of sodium azide (0.5 g) in 3 mL water was added dropwise, and the reaction mixture was stirred at ice bath temperature for 20 minutes. The reaction mixture was diluted with 100 mL toluene and washed with water. The organic layer was dried over MgSO$_4$, filtered, and concentrated under reduced pressure to give an oil, which was then dissolved in 100 mL toluene. The solution was heated to 100° C. for one hour, then cooled and concentrated under reduced pressure. The residue was dissolved in 15 mL dioxane, and the resulting solution was added dropwise to boiling 50% aqueous HCl. The mixture was refluxed for 15 minutes and then filtered while hot. The hot filtrate was cooled and the resulting precipitate was collected by filtration and dried to give 0.81 g of 2-[6-(3-fluoro-benzenesulfonyl)-naphthalen-1-yl]-ethylamine as a hydrochloride salt. MS (M+H)=330.

Example 4

3-[6-(3-Fluoro-benzenesulfonyl)-naphthalen-1-yl]-propylamine

The synthetic procedure described in this Example was carried out according to the process shown in Scheme H.

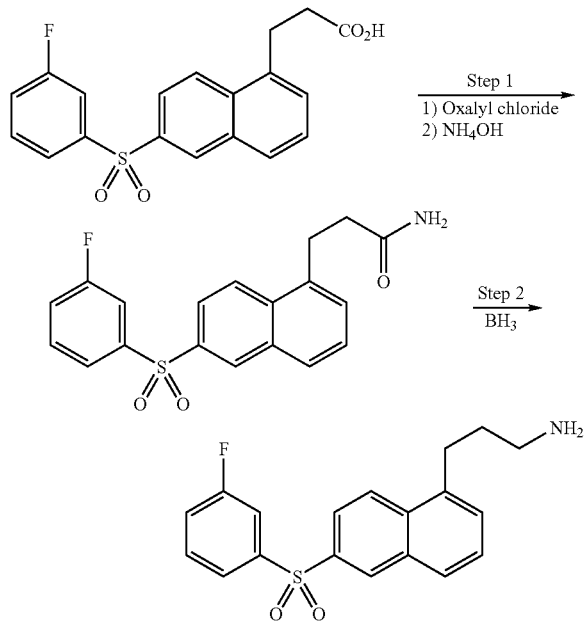

Step 1 3-[6-(3-Fluoro-benzenesulfonyl)-naphthalen-1-yl]-propionamide

To a suspension of 3-[6-(3-Fluoro-benzenesulfonyl)-naphthalen-1-yl]-propionic acid (1.0 g, 2.8 mmol) in 35 mL methylene chloride was added 0.8 mL oxalyl chloride. One drop of DMF was added, and the reaction mixture was stirred for 10 minutes at room temperature. The reaction mixture was concentrated under reduced pressure, and the resulting residue was dissolved in 10 mL EtOAc. This solution was added to stirring aqueous $NH_4OH$ (saturated) at ice bath temperature. The mixture was stirred for one hour, and then the organic layer was removed and the aqueous layer was extracted with EtOAc. The combined organic layers were dried over $MgSO_4$, filtered, and concentrated under reduced pressure to give 0.58 g of 3-[6-(3-fluoro-benzenesulfonyl)-naphthalen-1-yl]-propionamide. MS (M+H)=358.

Step 2 3-[6-(3-Fluoro-benzenesulfonyl)-naphthalen-1-yl]-propylamine

Borane (8 mL of 1M THF solution) was added to a solution of 3-[6-(3-fluoro-benzenesulfonyl)-naphthalen-1-yl]-propionamide in 20 mL THF. The reaction mixture was refluxed for five hours, then cooled and quenched by addition of 10% aqueous HCl (25 mL). The mixture was heated to reflux for one hour, then cooled and THF was removed under reduced pressure. The resulting precipitate was collected by filtration to give 0.42 g of 3-[6-(3-Fluoro-benzenesulfonyl)-naphthalen-1-yl]-propylamine. MS (M+H)=344.

Example 5

N-(6-Benzenesulfonyl-naphthalen-1-ylmethyl)-acetamidine

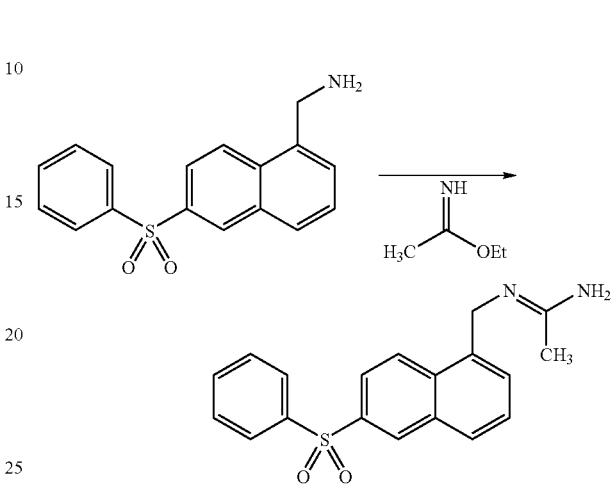

C-(6-benzenesulfonyl-naphthalen-1-yl)-methylamine and ethyl imidate (acetimidic acid ethyl ester) are dissolved in absolute ethanol, and the reaction mixture is stirred under argon at room temperature. Solvent is removed under reduced pressure, and the residue is recrystallized from $Et_2O$/EtOH to give N-(6-benzenesulfonyl-naphthalen-1-ylmethyl)-acetamidine as an oxalate salt.

Example 6

N-(6-Benzenesulfonyl-naphthalen-1-ylmethyl)-guanidine

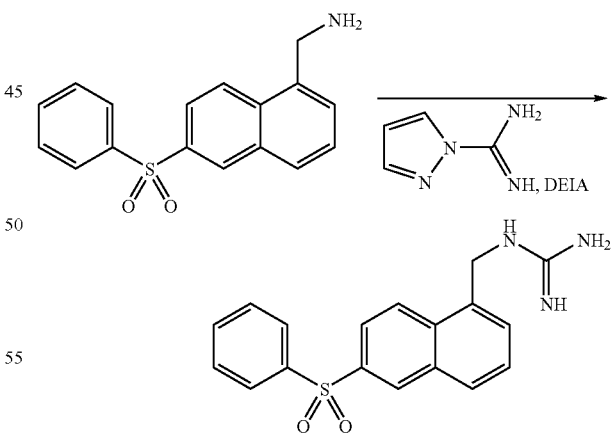

C-(6-Benzenesulfonyl-naphthalen-1-yl)-methylamine, 1H-pyrazol-1-carboxamidine hydrochloride and diethyl isopropylamine are dissolved in DMF, and the reaction mixture is heated to 100° C., then cooled and diluted by addition of water. The aqueous mixture is extracted with EtOAc, and the combined organic layers are dried over $MgSO_4$, filtered, and concentrated under reduced pressure to give N-(6-benzenesulfonyl-naphthalen-1-ylmethyl)-guanidine.

Example 7

(6-Benzenesulfonyl-naphthalen-1-ylmethyl)-(4,5-dihydro-1H-imidazol-2-yl)-amine

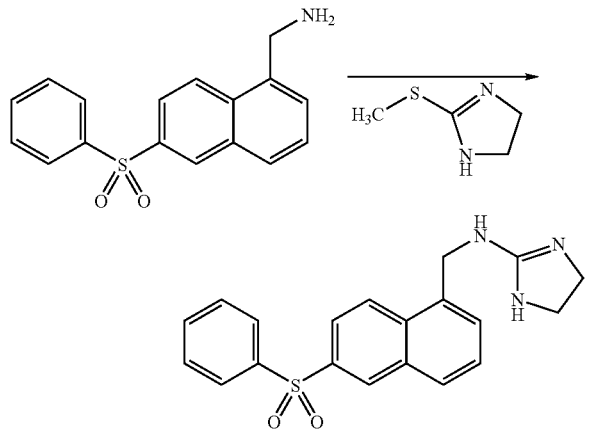

C-(6-Benzenesulfonyl-naphthalen-1-yl)-methylamine and 2-methylsulfanyl-4,5-dihydro-1H-imidazole hydroiodide were added to methylene chloride and the reaction mixture was heated to reflux until all of the solvent evaporates. The reaction mixture is heated to 150° C. and then cooled. The resulting mixture is basified by dropwise addition of aqueous NaOH solution, and then purified by preparative liquid chromatography to give (6-benzenesulfonyl-naphthalen-1-ylmethyl)-(4,5-dihydro-1H-imidazol-2-yl)-amine.

Example 8

(7-Benzenesulfonyl-naphthalen-1-ylmethyl)-(5,5-dimethyl-1,4,5,6-tetrahydro-pyrimidin-2-yl)-amine

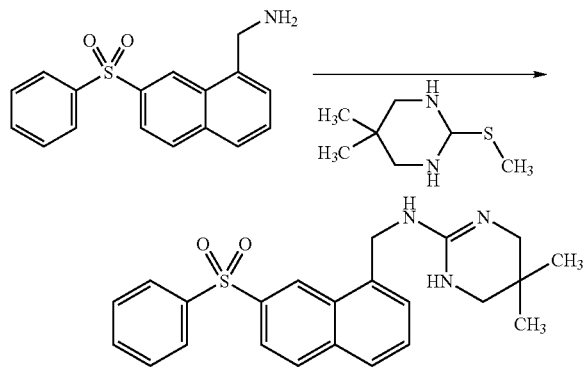

C-(6-Benzenesulfonyl-naphthalen-1-yl)-methylamine is prepared from 7-Benzenesulfonyl-3,4-dihydro-2H-naphthalen-1-one following the procedures of Examples 1 and 2. C-(6-Benzenesulfonyl-naphthalen-1-yl)-methylamine and 5,5-dimethyl-2-methylsulfanyl-hexahydro-pyrimidine hydrochloride are added to methylene chloride, and the reaction mixture is heated to gentle reflux until all of the solvent is evaporated. The reaction mixture is heated to 150° C. and then cooled. The resulting mixture is basified by dropwise addition of aqueous NaOH solution, and then purified by preparative liquid chromatography to give (7-benzenesulfonyl-naphthalen-1-ylmethyl)-(5,5-dimethyl-1,4,5,6-tetrahydro-pyrimidin-2-yl)-amine.

Example 9

N'-(6-Benzenesulfonyl-naphthalen-1-ylmethyl)-N,N-dimethyl-formamidine

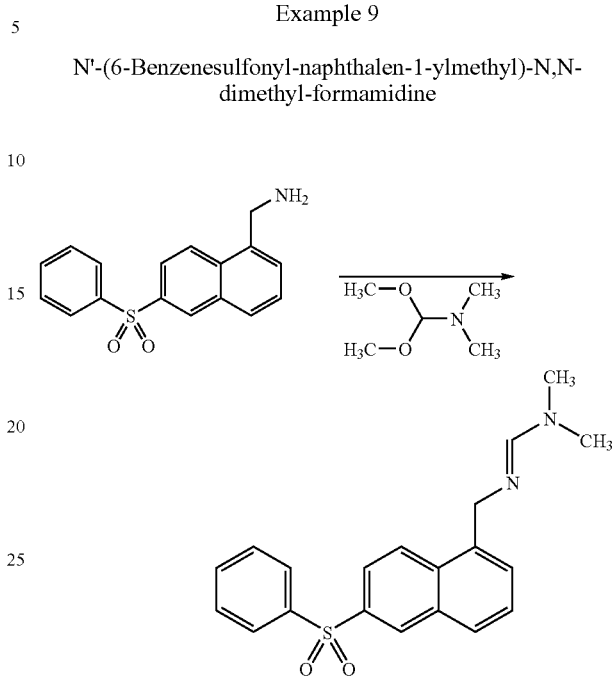

C-(6-Benzenesulfonyl-naphthalen-1-yl)-methylamine is added to dimethylformamide dimethyl acetal, and the reaction mixture is heated to 95° C. The reaction mixture is cooled and quenched by addition of water, and the resulting aqueous mixture is extracted with EtOAc. The organic layer is washed with water, brine, dried (MgSO$_4$), and evaporated under reduced pressure to give N'-(6-Benzenesulfonyl-naphthalen-1-ylmethyl)-N,N-dimethyl-formamidine.

Example 10

2-(6-Benzenesulfonyl-naphthalen-1-yl)-methyl]-dimethyl-amine

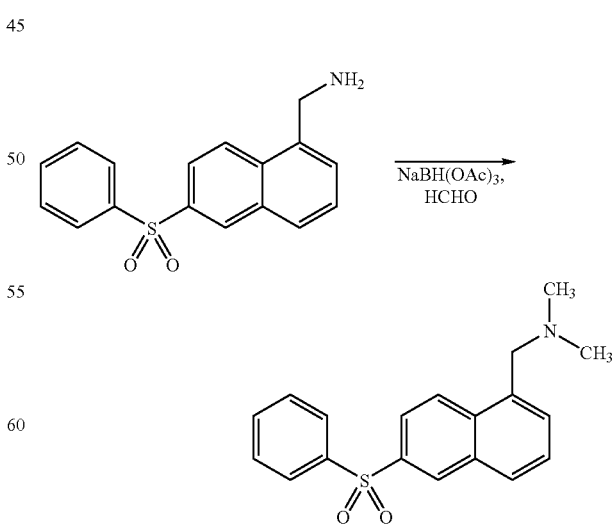

Using the procedure described *Journal of Organic Chemistry*, 61(11), 3849-3862 (1996), a solution of C-(6-benzenesulfonyl-naphthalen-1-yl)-methylamine and aqueous formaldehyde in methylene is stirred at room temperature, and NaBH(OAc)$_3$ is added and the reaction mixture is stirred at room temperature. Saturated aqueous NaHCO$_3$ is slowly added to quench the reaction, and the aqueous mixture is extracted with EtOAc. The organic layer is washed with water and brine, dried (MgSO$_4$), filtered, and concentrated under reduced pressure to afford 2-(6-benzenesulfonyl-naphthalen-1-yl)-methyl]-dimethyl-amine.

Example 11

N-(6-Benzenesulfonyl-naphthalen-1-ylmethyl)-acetamide

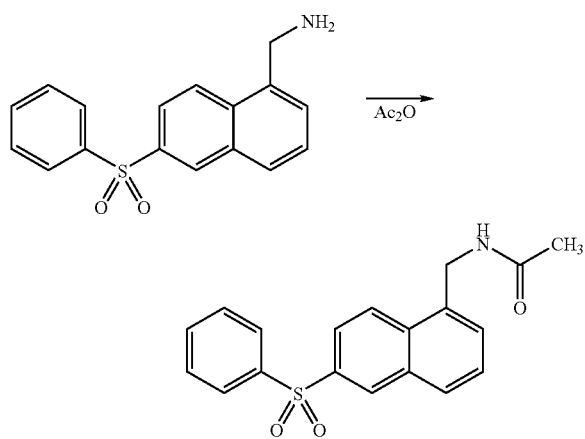

C-(6-Benzenesulfonyl-naphthalen-1-yl)-methylamine is dissolved in pyridine and acetyl chloride is added. The reaction mixture is stirred at room temperature and then quenched by addition of water. The mixture is extracted with EtOAc, and the organic layer is dried (MgSO$_4$), filtered, and concentrated under reduced pressure to give N-(6-benzenesulfonyl-naphthalen-1-ylmethyl)-acetamide.

Example 12

2-[(6-Benzenesulfonyl-naphthalen-1-ylmethyl)-amino]-3,5-dihydro-imidazol-4-one

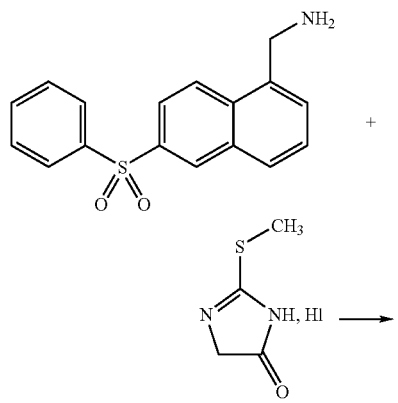

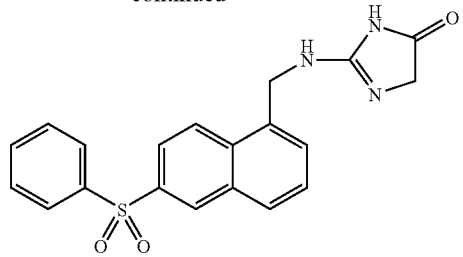

A mixture of C-(6-Benzenesulfonyl-naphthalen-1-yl)-methylamine, 2-methylsulfanyl-3,5-dihydro-imidazol-4-one (prepared by the method reported by Chen et al., WO9736859) and sodium hydroxide in ethanol is heated to reflux, then concentrated under reduced pressure, diluted with ethyl acetate, and washed with aqueous sodium carbonate. The organic phase is dried (magnesium sulfate) and concentrated under reduced pressure to give 2-[(6-benzenesulfonyl-naphthalen-1-ylmethyl)-amino]-3,5-dihydro-imidazol-4-one.

Example 13

N-(6-Benzenesulfonyl-naphthalen-1-ylmethyl)-2-methylamino-acetamide

The synthetic procedure described in this Example was carried out according to the process shown in Scheme I.

SCHEME I

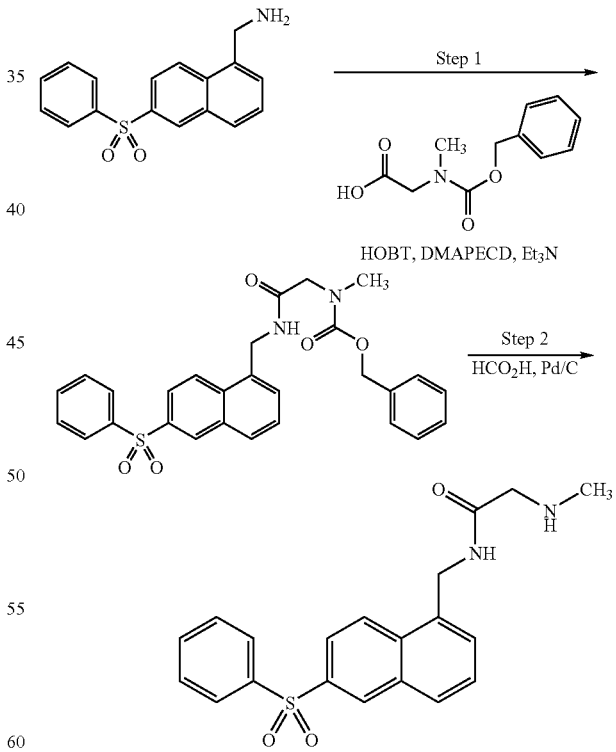

Step 1 {[(6-Benzenesulfonyl-naphthalen-1-ylmethyl)-carbamoyl]-methyl}-methyl-carbamic acid benzyl ester A mixture of C-(6-benzenesulfonyl-naphthalen-1-yl)-methylamine, (Benzyloxycarbonyl-methyl-amino)-acetic acid, 1-hydroxybenzotriazole, N-(3-dimethylaminopropyl)-N-ethylcarbodiimide and triethylamine in methylene chloride is stirred at room temperature. The reaction is quenched by addition of water, and the mixture is eluted through silica gel to give {[(6-Benzenesulfonyl-naphthalen-1-ylmethyl)-carbamoyl]-methyl}-methyl-carbamic acid benzyl ester.

Step 2 N-(6-Benzenesulfonyl-naphthalen-1-ylmethyl)-2-methylamino-acetamide

To a stirring solution of {[(6-Benzenesulfonyl-naphthalen-1-ylmethyl)-carbamoyl]-methyl}-methyl-carbamic acid benzyl ester in methanol and formic acid at room temperature is added palladium on carbon. The mixture is stirred at room temperature, filtered thru Celite, and the filtrate is concentrated to give N-(6-benzenesulfonyl-naphthalen-1-ylmethyl)-2-methylamino-acetamide.

Example 14

2-[(6-Benzenesulfonyl-naphthalen-1-ylmethyl)-amino]-N-methyl-acetamide

The synthetic procedure described in this Example was carried out according to the process shown in Scheme J.

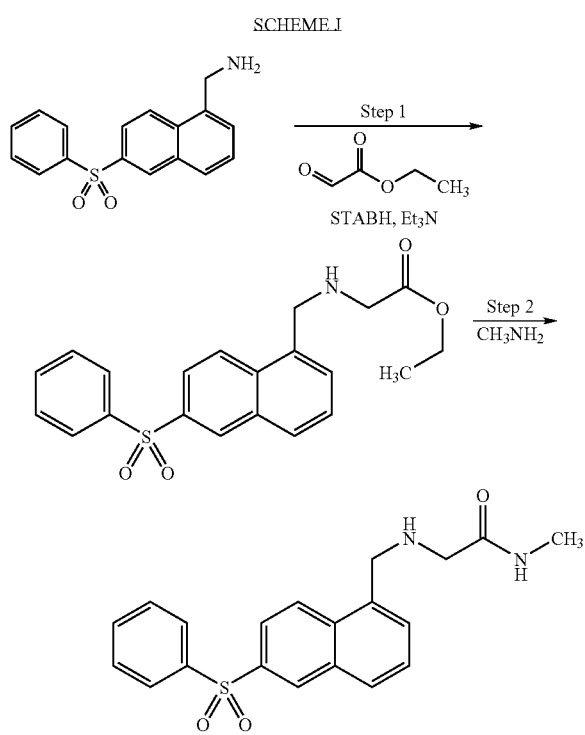

Step 1 [(6-Benzenesulfonyl-naphthalen-1-ylmethyl)-amino]-acetic acid ethyl ester C-(6-Benzenesulfonyl-naphthalen-1-yl)-methyl amine and triethyl amine (0.2 ml, 1.55 mmole) in dichloroethane are stirred and cooled in an ice-bath. Ethylgloxylate is added, followed by sodium triacetoxyborohydride. The reaction is stirred and then quenched by addition of 2% sodium carbonate solution. The mixture is extracted with ethyl acetate, and the organic layer is dried over magnesium sulfate, filtered, and concentrated under reduced pressure to give [(6-benzenesulfonyl-naphthalen-1-ylmethyl)-amino]-acetic acid ethyl ester

Step 2 2-[(6-Benzenesulfonyl-naphthalen-1-ylmethyl)-amino]-N-methyl-acetamide

[(6-Benzenesulfonyl-naphthalen-1-ylmethyl)-amino]-acetic acid ethyl ester is added to methylamine in methanol, and the solution is stirred at room temperature, then concentrated under reduced pressure. The oil is dissolved in ethanol and 1N HCl in diethyl ether is added to precipitate 2-[(6-benzenesulfonyl-naphthalen-1-ylmethyl)-amino]-N-methyl-acetamide as a hydrochloride salt.

Example 15

(6-Benzenesulfonyl-naphthalen-1-ylmethyl)-urea

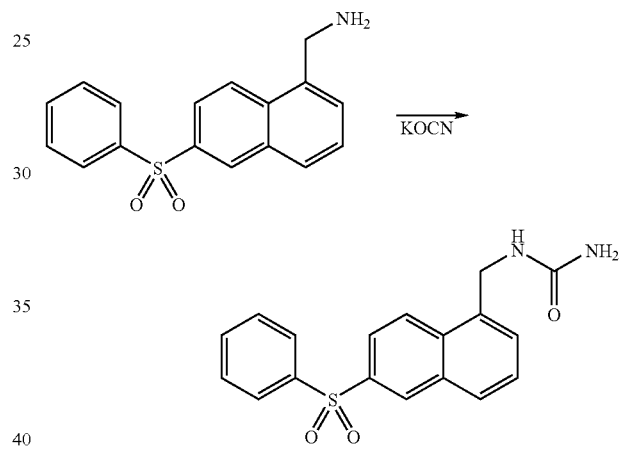

C-(6-Benzenesulfonyl-naphthalen-1-yl)-methylamine and potassium cyanate are added to stirring water, and the mixture is heated to 60° C., then cooled to room temperature. The resulting precipitate is collected by filtration, washed with cold water, and dried under vacuum to give (6-benzenesulfonyl-naphthalen-1-ylmethyl)-urea.

Example 16

N-(6-Benzenesulfonyl-naphthalen-1-ylmethyl)-methanesulfonamide

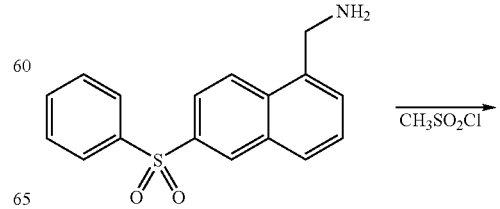

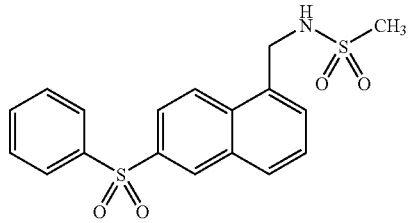

C-(6-Benzenesulfonyl-naphthalen-1-yl)-methylamine is dissolved in methylene chloride and pyridine, and the mixture is cooled in an ice bath. Methanesulfonyl chloride is added dropwise, and the reaction mixture is stirred at ice bath temperature, then allowed to warm to room temperature. The reaction mixture is quenched by addition of water and extracted with methylene chloride. The organic layer is washed with water, dried (MgSO$_4$), filtered and concentrated under reduced pressure to give N-(6-benzenesulfonyl-naphthalen-1-ylmethyl)-methanesulfonamide.

Example 17

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |

| Composition for Oral Administration | |
|---|---|
| Ingredient | Amount |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 18

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-$HT_{2A}$ ligand affinity were made by competing for binding of [$^3$H]Ketanserin (3-(2-(4-(4-fluorobenzoyl)piperidinol)ethyl)-2,4(1H, 3H)-quinazolinedione) in cell membranes derived from CHO-K1 cells stably expressing recombinant human 5-$HT_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J. Pharmacol. June; 115(4): 622-8 (1995).

For estimation of affinity at the 5-$HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the 5-$HT_{2A}$ receptor all determinations were made in assay buffer containing 50 mM Tris-HCl, 5 mM ascorbic acid, 4 mM $CaCl2$, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-$HT_6$) or 60 min. at 32° C. (for 5-$HT_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-Hill(\log[\text{ligand}] - \log IC_{50})}} \right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters.

Using the procedures of this Example, compounds of Formula I were tested and found to be selective 5-$HT_6$ antagonists, selective 5-$HT_{2A}$ antagonists, or both. For example, the compound (6-Benzenesulfonyl-naphthalen-1-ylmethyl)-methyl-amine exhibited a pKi of approximately 9.35 for 5-$HT_6$, and C-[6-(3-Fluoro-benzenesulfonyl)-naphthalen-1-yl]-methylamine exhibited a pKi of approximately 8.3 for 5-$HT_{2A}$.

Example 19

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I:

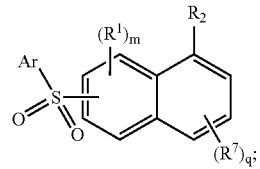

or a pharmaceutically acceptable salt thereof,
wherein:
m is from 0 to 3;
q is from 0 to 3;
Ar is optionally substituted aryl or optionally substituted heteroaryl;
$R^1$ and $R^7$ each independently is halo, alkyl, haloalkyl, alkoxy, hydroxy, heteroalkyl, cyano, —S(O)$_t$—$R^a$, —C(=O)—$NR^bR^c$, —$SO_2$—$NR^bR^c$, —N($R^d$)—C(=O)—$R^e$, or —C(=O)—$R^f$, where t is from 0 to 2, $R^a$, $R^b$, $R^c$, $R^d$ and $R^e$ each independently is hydrogen or alkyl, and $R^f$ is hydrogen, alkyl, alkoxy or hydroxy;
$R^2$ is

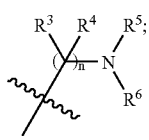

n is from 1 to 3;
$R^3$ and $R^4$ each independently is hydrogen or alkyl, or $R^3$ and $R^4$ together may form =O or =$NR^z$ wherein $R^z$ is hydrogen or alkyl; and one of R⁵ and R⁶ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; alkylsulfonylalkyl; or optionally substituted heteroaryl; or R⁵ and R⁶ together with the nitrogen to which they are attached may form an amidinyl group, a urea group, a guanidinyl group or a five- or six-membered heteroaryl or heterocyclyl ring that is optionally substituted and which optionally includes an additional heteroatom selected from O, N and S; or one of R⁵ and R⁶ and one of R³ and R⁴ together with the atoms to which they are attached may form a five- or six-membered ring that optionally includes an additional heteroatom selected from O, N and S.

2. The compound of claim 1, wherein the group Ar—SO₂— is located at the 6-position of the naphthalene ring system.

3. The compound of claim 1, wherein n is 1.

4. The compound of claim 3, wherein R³ and R⁴ are hydrogen.

5. The compound of claim 4, wherein one of R⁵ and R⁶ is hydrogen and the other is alkyl.

6. The compound of claim 3, wherein q is 0.

7. The compound of claim 3, wherein R⁵ and R⁶ are hydrogen.

8. The compound of claim 1, wherein q is 0, m is 0 or 1, R³ and R⁴ are hydrogen, one of R⁵ and R⁶ is hydrogen or alkyl, and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

9. The compound of claim 1, wherein q is 0, m is 0 or 1, R³ and R⁴ are hydrogen, one of R⁵ and R⁶ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

10. The compound of claim 1, wherein q is 0, m is 0 or 1, R³ and R⁴ are hydrogen, one of R⁵ and R⁶ is hydrogen and the other is alkyl.

11. The compound of claim 1, wherein q is 0, m is 0 or 1, n is 1, and R² is: aminoalkyl; alkylaminoalkyl; dialkylaminoalkyl; imidazolinylaminoalkyl; imidazolinylalkyl, guanidinylalkyl; tetrahydropyrimidinylaminoalkyl; amidinylalkyl; urealkyl; amidinyl; heteroarylaminoalkyl; imidazolylaminoalkyl; guanidinylcarbonylalkyl; imidazolonylaminoalkyl; imidazolinylcarbonylaminoalkyl; aminocarbonylalkyl; pyrrolylcarbonylaminoalkyl; aminoalkylcarbonylaminoalkyl; alkoxycarbonylalkylaminoalkyl; N-cyanoguanidinylalkyl; alkylcarbonylaminoalkyl; aminocarbonylalkylaminoalkyl; pyrrolidinylcarbonylaminoalkyl; alkylsulfonamidoalkyl; aminosulfonamidoalkyl; alkoxycarbonylaminoalkyl; hydroxyalkylcarbonylaminoalkyl; hydroxyalkylaminoalkyl; alkoxyalkylaminoalkyl; or alkylsulfonylalkylaminoalkyl.

12. The compound of claim 1, wherein q is 0, m is 0 or 1, and R² is: aminoalkyl; alkylaminoalkyl; dialkylaminoalkyl; guanidinylalkyl; amidinylalkyl; urealkyl; amidinyl; guanidinylcarbonylalkyl; aminocarbonylalkyl; aminoalkylcarbonylaminoalkyl; alkylcarbonylaminoalkyl; aminocarbonylalkylaminoalkyl; or alkoxycarbonylaminoalkyl.

13. The compound of claim 1, wherein q is 0, m is 0 or 1, and R² is:

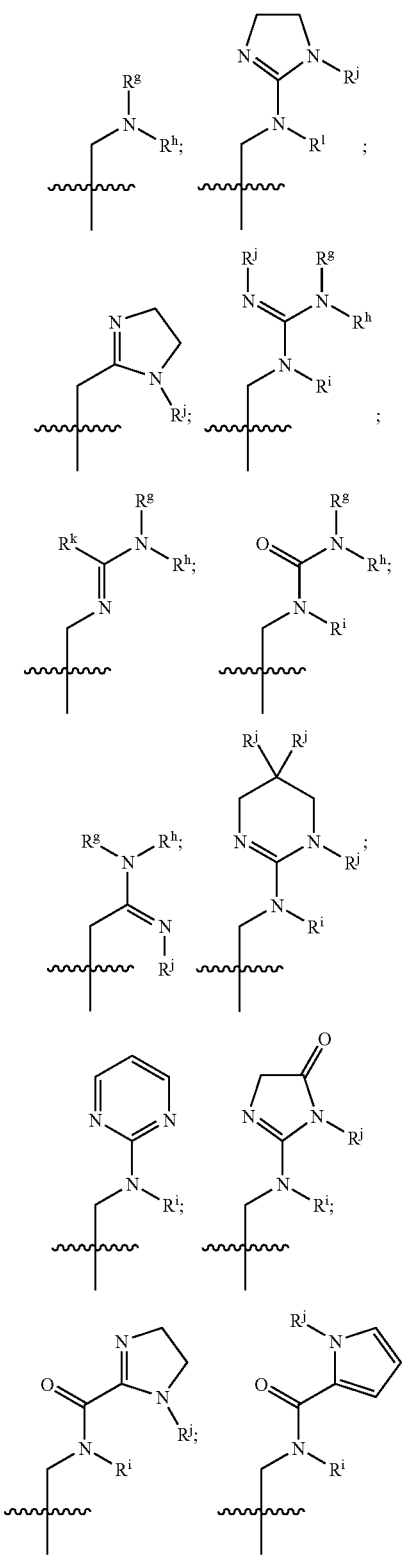

-continued
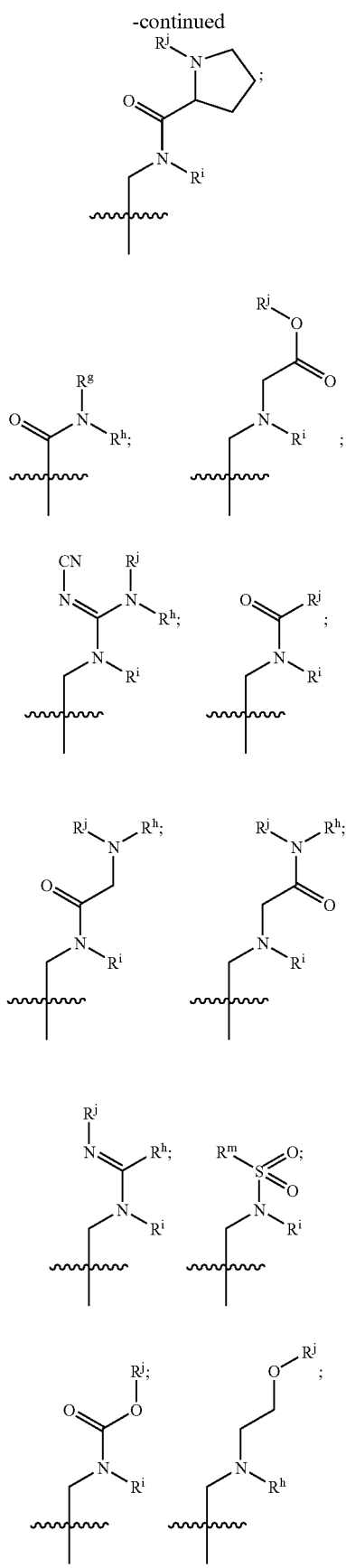
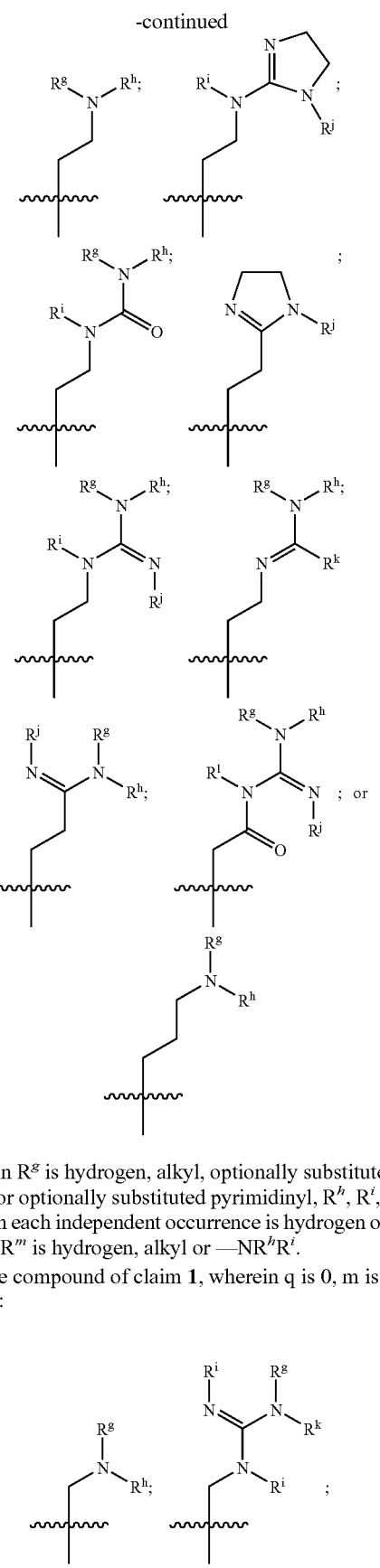
wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.
14. The compound of claim 1, wherein q is 0, m is 0 or 1, and $R^2$ is:
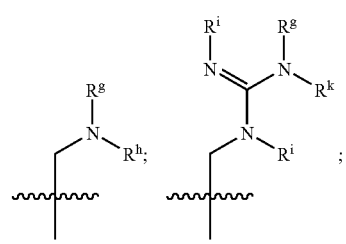

-continued

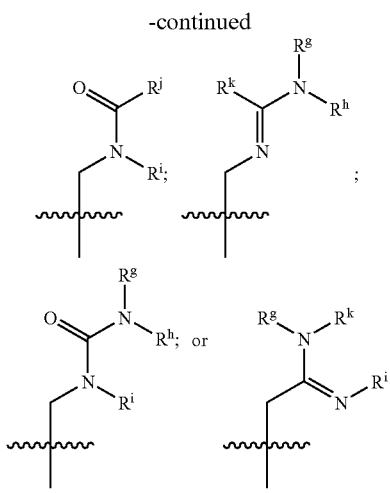

wherein $R^h$ is hydrogen, alkyl or alkylsulfonyl, $R^j$ is hydrogen, alkyl or amino, and $R^g$, $R^i$ and $R^k$
$R^g$, $R^h$, $R^i$ and $R^j$ are hydrogen or alkyl.

15. The compound of claim 1, wherein q is 0, m is 0 or 1, n is 1, $R^3$ and $R^4$ are hydrogen, one of $R^5$ and $R^6$ is hydrogen or alkyl, and the other is:

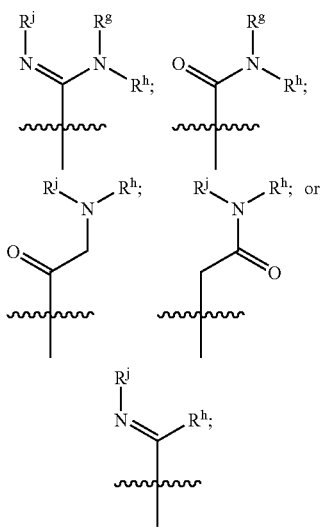

wherein $R^g$, $R^h$, $R^i$ and $R^j$ are hydrogen or alkyl.

16. The compound of claim 1, wherein said compound is of formula II:

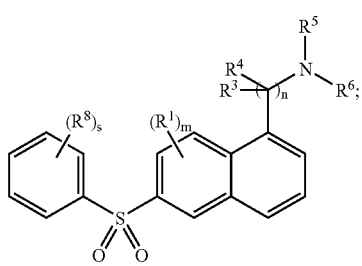

wherein:
s is from 0 to 4;
each $R^8$ is independently halo, alkyl, alkoxy, haloalkyl, heteroalkyl, cyano, —S(O)$_r$—$R^a$, —C(=O)—NR$^b$R$^c$, —SO$_2$—NR$^b$R$^c$, —N(R$^d$)—C(=O)—R$^e$, or —C(=O)—R$^c$, where r is from 0 to 2, $R^a$, $R^b$, $R^c$ and $R^d$ each independently is hydrogen or alkyl, and $R^e$ is hydrogen, alkyl, alkoxy or hydroxy; and
m, n, $R^1$, $R^3$, $R^4$, $R^5$ and $R^6$ are as defined herein.

17. The compound of claim 1, wherein said compound is of formula III:

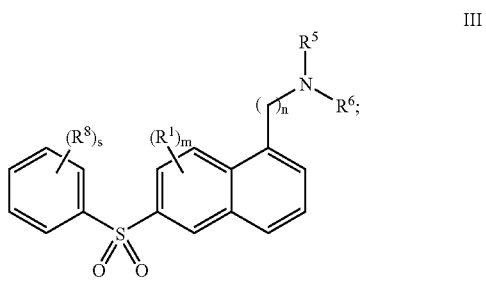

wherein m, n, s, $R^1$, $R^5$, $R^6$ and $R^8$ are as defined herein.

18. The compound of claim 1, wherein said compound is selected from:
(6-Benzenesulfonyl-naphthalen-1-ylmethyl)-methyl-amine;
C-[6-(3-Fluoro-benzenesulfonyl)-naphthalen-1-yl]-methylamine;
N-[6-(3-Fluoro-benzenesulfonyl)-naphthalen-1-ylmethyl]-acetamide;
[6-(3-Fluoro-benzenesulfonyl)-naphthalen-1-ylmethyl]-urea;
Ethanesulfonic acid [6-(3-fluoro-benzenesulfonyl)-naphthalen-1-ylmethyl]-amide;
2-[6-(3-Fluoro-benzenesulfonyl)-naphthalen-1-yl]-ethylamine;
3-[6-(3-Fluoro-benzenesulfonyl)-naphthalen-1-yl]-propionamide;
{2-[6-(3-Fluoro-benzenesulfonyl)-naphthalen-1-yl]-ethyl}-urea;
N-{2-[6-(3-Fluoro-benzenesulfonyl)-naphthalen-1-yl]-ethyl}-acetamide;
{3-[6-(3-Fluoro-benzenesulfonyl)-naphthalen-1-yl]-propyl}-urea;
3-[6-(3-Fluoro-benzenesulfonyl)-naphthalen-1-yl]-propylamine;
N-{2-[6-(3-Fluoro-benzenesulfonyl)-naphthalen-1-yl]-ethyl}-methanesulfonamide;
N-{3-[6-(3-Fluoro-benzenesulfonyl)-naphthalen-1-yl]-propyl}-acetamide; and
4-[6-(3-Fluoro-benzenesulfonyl)-naphthalen-1-ylmethyl]-piperazin-2-one.

19. A pharmaceutical composition comprising an effective amount of the compound of claim 1 in admixture with a pharmaceutically acceptable carrier.

20. A method for enhancing cognitive memory in an Alzheimer's patient, said method comprising administering to said patient a therapeutically effective amount of a compound of claim 1.

* * * * *